(12) United States Patent
Miller-Jones et al.

(10) Patent No.: US 11,519,916 B2
(45) Date of Patent: *Dec. 6, 2022

(54) METHODS FOR ANALYSING A URINE SAMPLE

(71) Applicant: ARQUER DIAGNOSTICS LIMITED, Sunderland (GB)

(72) Inventors: David Nicholas Miller-Jones, Sunderland (GB); Jacqueline Stockley, Sunderland (GB); Cheryl Nyberg, Sunderland (GB)

(73) Assignee: ARQUER DIAGNOSTICS LIMITED, Sunderland (GB)

( * ) Notice: Subject to any disclaimer, the term of this patent is extended or adjusted under 35 U.S.C. 154(b) by 691 days.

This patent is subject to a terminal disclaimer.

(21) Appl. No.: 15/580,657

(22) PCT Filed: Jun. 1, 2016

(86) PCT No.: PCT/GB2016/051608
§ 371 (c)(1),
(2) Date: Dec. 7, 2017

(87) PCT Pub. No.: WO2016/198833
PCT Pub. Date: Dec. 15, 2016

(65) Prior Publication Data
US 2018/0203012 A1    Jul. 19, 2018

(30) Foreign Application Priority Data

Jun. 8, 2015 (GB) .................................. 1509909
Mar. 1, 2016 (GB) .................................. 1603559

(51) Int. Cl.
| | | |
|---|---|---|
| G01N 33/53 | (2006.01) | |
| G01N 33/574 | (2006.01) | |
| G01N 1/34 | (2006.01) | |
| G01N 1/40 | (2006.01) | |

(52) U.S. Cl.
CPC ......... *G01N 33/57434* (2013.01); *G01N 1/34* (2013.01); *G01N 1/40* (2013.01); *G01N 33/574* (2013.01); *G01N 2001/4088* (2013.01)

(58) Field of Classification Search
None
See application file for complete search history.

(56) References Cited

U.S. PATENT DOCUMENTS

| | | |
|---|---|---|
| 4,022,576 A | 5/1977 | Parker |
| 4,868,108 A | 9/1989 | Bahar et al. |
| 5,016,644 A | 5/1991 | Guirguis |
| 5,087,556 A | 2/1992 | Ertinghausen |
| 6,008,003 A | 12/1999 | Haak-Frendscho et al. |
| 6,812,339 B1 | 11/2004 | Venter et al. |
| 7,498,145 B2 | 3/2009 | Uchiyama et al. |
| 7,842,467 B1 | 11/2010 | Heidbrink et al. |
| 7,932,047 B2 | 4/2011 | Ridder et al. |
| 8,062,892 B2 | 11/2011 | Schlegel et al. |
| 8,158,360 B2 | 4/2012 | Heise et al. |
| 8,193,332 B2 | 6/2012 | Takagi et al. |
| 8,344,211 B2 | 1/2013 | Alexandrov et al. |
| 8,470,798 B2 | 6/2013 | Takagi et al. |
| 8,497,101 B2 | 7/2013 | Mechali et al. |
| 8,652,416 B2 | 2/2014 | Kim et al. |
| 2004/0241876 A1 | 12/2004 | Fannes |
| 2005/0069900 A1 | 3/2005 | Lentrichia |
| 2005/0208558 A1 | 9/2005 | Venter et al. |
| 2006/0088840 A1 | 4/2006 | Giesing et al. |
| 2007/0037165 A1 | 2/2007 | Venter et al. |
| 2007/0184460 A1 | 8/2007 | Ching et al. |
| 2007/0184505 A1* | 8/2007 | Schmitt ............... G01N 1/30 435/7.92 |
| 2007/0237770 A1 | 10/2007 | Lai et al. |
| 2009/0088336 A1 | 4/2009 | Burd et al. |
| 2009/0226957 A1 | 9/2009 | Paterlini-Brechot |
| 2010/0015625 A1 | 1/2010 | Indra et al. |
| 2010/0094560 A1 | 4/2010 | Lois et al. |
| 2010/0240546 A1 | 9/2010 | Lo et al. |
| 2010/0240665 A1 | 9/2010 | Eckhardt et al. |
| 2011/0093962 A1 | 4/2011 | Heidbrink et al. |

(Continued)

FOREIGN PATENT DOCUMENTS

| | | |
|---|---|---|
| AU | 2011236061 A1 | 11/2011 |
| CA | 2040088 A1 | 10/1992 |

(Continued)

OTHER PUBLICATIONS

Abeam (1999;retrieved from url://www.abcam.com/protocols/sample-preparation-for-western-blot).*
Gutierez et al.(2012, retrieved from url.emdmillipore.com).*
International Search Report issued in connection with corresponding International Application No. PCT/GB2016/051611, dated Sep. 23, 2016, 2 pages.
Altschul et al., "Basic local alignment search tool", Oct. 1990; 215(3): 403-410.
Ayaru L et al., "Diagnosis of pancreaticobiliary malignancy by detection of minichromosome maintenance protein 5 in bile aspirates," British Journal of Cancer (2008) 98, 1548-1554.
Bauminger S et al., "The use of carbodiimides in the preparation of immunizing conjugates", Methods Enzymol. 1980; 70(A): 151-9.

(Continued)

*Primary Examiner* — Gary Counts
(74) *Attorney, Agent, or Firm* — Kilpatrick Townsend & Stockton LLP

(57) ABSTRACT

The present invention provides methods for analysing a urine sample from a subject comprising exposing the urine sample to a lysis buffer which is capable of releasing at least one biomarker from cells in the urine sample. The present invention further provides kits, devices, and apparatuses that can be used in these methods. Finally, the present invention provides methods for detecting the presence of a urological cancer in a subject comprising performing an assay on a sample from a subject to determine the concentration of an Mcm protein.

6 Claims, 22 Drawing Sheets

Specification includes a Sequence Listing.

(56) References Cited

U.S. PATENT DOCUMENTS

| | | | |
|---|---|---|---|
| 2012/0039811 A1* | 2/2012 | Admon | A61K 39/0011 424/9.1 |
| 2012/0070837 A1 | 3/2012 | Huang et al. | |
| 2012/0190046 A1 | 7/2012 | Datta et al. | |
| 2013/0034869 A1 | 2/2013 | Whitesides et al. | |
| 2013/0115599 A1 | 5/2013 | Huang et al. | |
| 2013/0237453 A1 | 9/2013 | Chander | |

FOREIGN PATENT DOCUMENTS

| | | |
|---|---|---|
| CN | 101358976 A | 2/2009 |
| CN | 101738469 A | 6/2010 |
| CN | 101993926 A | 3/2011 |
| CN | 102375061 A | 3/2012 |
| CN | 102707063 A | 10/2012 |
| CN | 103558384 A | 2/2014 |
| DE | 10316701 A1 | 11/2004 |
| DE | 10054632 A1 | 7/2007 |
| EP | 0217583 B1 | 4/1987 |
| EP | 0225054 B1 | 6/1987 |
| EP | 0509158 A1 | 10/1992 |
| EP | 0763738 A1 | 3/1997 |
| EP | 1388734 A1 | 2/2004 |
| EP | 1510820 A1 | 3/2005 |
| EP | 1628135 A1 | 2/2006 |
| EP | 1816460 A1 | 8/2007 |
| EP | 1916301 A1 | 4/2008 |
| EP | 1980856 A1 | 10/2008 |
| EP | 2138848 A1 | 12/2009 |
| EP | 2196803 A1 | 6/2010 |
| EP | 2434023 A1 | 3/2012 |
| EP | 2574400 A1 | 4/2013 |
| JP | 200580524 A | 3/2005 |
| JP | 2005315772 A2 | 11/2005 |
| JP | 20095655 A | 1/2009 |
| JP | 201088376 A | 4/2010 |
| JP | 2012196211 A | 10/2012 |
| KR | 1020150105167 A | 9/2015 |
| RU | 2456607 C1 | 7/2012 |
| RU | 2470301 C2 | 9/2012 |
| RU | 2463354 C1 | 10/2012 |
| WO | WO 9921014 A1 | 4/1999 |
| WO | WO 0026242 A2 | 5/2000 |
| WO | WO 0029852 A1 | 5/2000 |
| WO | WO 0039586 A2 | 7/2000 |
| WO | WO 0059943 A2 | 10/2000 |
| WO | WO 0102599 A2 | 1/2001 |
| WO | WO 0111361 A2 | 2/2001 |
| WO | WO 0171042 A2 | 9/2001 |
| WO | WO 02087641 A2 | 11/2002 |
| WO | WO 03024993 A2 | 3/2003 |
| WO | WO 03072035 A2 | 9/2003 |
| WO | WO 04023973 A2 | 3/2004 |
| WO | WO 04030615 A2 | 4/2004 |
| WO | WO 04035783 A2 | 4/2004 |
| WO | WO 04038418 A1 | 5/2004 |
| WO | WO 04039956 A2 | 5/2004 |
| WO | WO 04043361 A2 | 5/2004 |
| WO | WO 04092734 A2 | 10/2004 |
| WO | WO 05026211 A2 | 3/2005 |
| WO | WO 05084283 A2 | 9/2005 |
| WO | WO 05085860 A2 | 9/2005 |
| WO | WO 05095964 A2 | 10/2005 |
| WO | WO 05097189 A1 | 10/2005 |
| WO | WO 06039582 A2 | 4/2006 |
| WO | WO 06052822 A2 | 5/2006 |
| WO | WO 06071970 A2 | 7/2006 |
| WO | WO 06086573 A2 | 8/2006 |
| WO | WO 06116442 A2 | 11/2006 |
| WO | WO 06126821 A1 | 11/2006 |
| WO | WO 07031789 A1 | 3/2007 |
| WO | WO 07042256 A1 | 4/2007 |
| WO | WO 07045896 A1 | 4/2007 |
| WO | WO 07110314 A2 | 10/2007 |
| WO | WO 08021290 A2 | 2/2008 |
| WO | WO 08043566 A2 | 4/2008 |
| WO | WO 08085007 A1 | 7/2008 |
| WO | WO 08132453 A1 | 11/2008 |
| WO | WO 09002849 A2 | 12/2008 |
| WO | WO 09020596 A2 | 2/2009 |
| WO | WO 09050461 A1 | 4/2009 |
| WO | WO 09138392 A1 | 11/2009 |
| WO | WO 09145815 A2 | 12/2009 |
| WO | WO 09156711 A1 | 12/2009 |
| WO | WO 10025928 A1 | 3/2010 |
| WO | WO 10042228 A2 | 4/2010 |
| WO | WO 10107654 A2 | 9/2010 |
| WO | WO 11073619 A1 | 6/2011 |
| WO | WO 11082345 A2 | 7/2011 |
| WO | WO 11109705 A2 | 9/2011 |
| WO | WO 11126482 A1 | 10/2011 |
| WO | WO 11129762 A1 | 10/2011 |
| WO | WO 11133981 A1 | 10/2011 |
| WO | WO 12065117 A2 | 5/2012 |
| WO | WO 12090479 A1 | 7/2012 |
| WO | WO 12093251 A1 | 7/2012 |
| WO | WO 12109466 A2 | 8/2012 |
| WO | WO 12151465 A1 | 11/2012 |
| WO | WO 13071247 A1 | 5/2013 |
| WO | WO 13102757 A1 | 7/2013 |
| WO | WO 13120394 A1 | 8/2013 |
| WO | WO 13121368 A2 | 8/2013 |
| WO | WO 13151672 A2 | 10/2013 |
| WO | WO 13181418 A2 | 12/2013 |
| WO | WO 13190075 A2 | 12/2013 |
| WO | WO 14012176 A1 | 1/2014 |
| WO | WO 14025961 A1 | 2/2014 |
| WO | WO 14032899 A1 | 3/2014 |
| WO | WO 14065889 A2 | 5/2014 |
| WO | WO 14071029 A1 | 5/2014 |
| WO | WO 14077725 A1 | 5/2014 |
| WO | WO 14081278 A1 | 5/2014 |
| WO | WO 16112501 A1 | 7/2015 |

OTHER PUBLICATIONS

Burger M, "MCM2 and MCM5 as prognostic markers in colon cancer: a worthwhile approach", Dig Dis Sci. Feb. 2009; 54(2): 197-8.

Chun FK et al., "Prostate cancer gene 3 (PCA3): development and internal validation of a novel biopsy nomogram", Eur Urol. Oct. 2009; 56(4): 659-67.

Devereux et al., "A comprehensive set of sequence analysis programs for the VAX", Nucleic Acids Research Jan. 1984; 12(1): 387-395.

Dudderidge TJ et al., "Diagnosis of prostate cancer by detection of minichromosome maintenance 5 protein urine sediments", Br J Cancer. Aug. 2010; 103(5): 701-7.

Going JJ et al., "Aberrant expression of minichromosome maintenance proteins 2 and 5, and Ki-67 in dysplastic squamous oesophageal epithelium and Barrett's mucosa," Gut 2002;50:373-377.

Gonzalez MA et al., "New Minimally Invasive Approaches to Early Cancer Detection", European Oncological Disease. 2007; 1(2): 122-4.

Herr HW, "The natural history of a T1 bladder cancer: life-long tumour diathesis", BJU Int. 1999; 84: 1102-1103.

Hessels D & Schalken JA, "The use of PCA3 in the diagnosis of prostate cancer", Nat Rev Urol. May 2009; 6(5): 255-61.

Jemal A et al., "Cancer statistics, 2007", CA Cancer J Clin. Jan.-Feb. 2007; 57(1): 43-66.

Karakiewizc et al., "Critical evaluation of urinary markers for bladder cancer detection and monitoring", Rev Urol, 2008 Spring; 10(2): 120-135.

Kelly JD et al., "Bladder cancer diagnosis and identification of clinically significant disease by combined urinary detection of Mcm6 and nuclear matrix protein 22", PLoS One. 2012; 7(7): e40305.

Kilpelainen TP et al., "False-positive screening results in the Finnish prostate cancer screening trial", Br J Cancer. Feb. 2010; 102(3): 469-74.

(56) References Cited

OTHER PUBLICATIONS

Scarpini Cinzia et al., "Improved Screening for Anal Neoplasia by Immunocytochemical Detection of Minichromosome Maintenance Proteins," Cancer Epidemiol Biomarkers Prev 2008;17(10). Oct. 2008.
Stoeber K et al., "Diagnosis of Genito-Urinary Tract Cancer by Detection of Minichromosome Maintenance 5 Protein in Urine Sediments", J of the Nat Cancer Inst. Jul. 2002; 94(14): 1071-79.
Stoeber K et al., "Immunoassay for urothelial cancers that detects DNA replication protein Mcm5 in urine", The Lancet, vol. 354, Oct. 30, 1999, 1524-1525.
Swinn RA. "Immunoassay for minichromosome maintenance protein Mcm5 in cancer detection", MPhil Thesis submitted to Anglia Polytechnic University in Nov. 2004.
Thompson IM et al., "Operating characteristics of prostate-specific antigen in men with an initial PSA level of 3.0 ng.ml or lower", JAMA. Jul. 2005; 294(1): 66-71.
Thomson JD et al. "CLUSTAL W: improving the sensitivity of progressive multiple sequence alignment through sequence weighting, position-specific gap penalties and weight matrix choice", Nucleic Acids Res. 1994; 22:4673-4680.
Van Der Poel HG & Debruyne FB, "Can biological markers replace cystoscopy? An update", Curr Opin Urol. Oct. 2001; 11(5): 503-9.
Watkins JL, "An investigation into minichromosomal maintenance proteins (MCMs) for the diagnosis of prostate cancer, as a possible alternative to prostate specific antigen (PSA)", Feb. 2005. Retrieved from the Internet <URL:https://dspace.lib.cranfield.ac.uk/bitstream/1826/1643/1/JaneWatkinsPhDThesis.pdf> [retrieved on Jan. 27, 2015] 200 pages.
Wiener HG et al., "Accuracy of urinary cytology in the diagnosis of primary and recurrent bladder cancer", Acta Cytol. Mar.-Apr. 1993; 37(2): 163-9.
Williams GH et al., "Diagnosis of oesophageal cancer by detection of minichromosome maintenance 5 protein in gastric aspirates", BJC. Aug. 2004; 91(4): 714-9.
Kelly et al., Bladder Cancer Diagnosis and Identification of Clinically Significant Disease by Combined Urinary Detection of Mcm5 and Nuclear Matrix Protein 22, PLOS One, 2012, 7(7), e40305, pp. 1-9.
PerkinElmer product brochure, "Applications of time-resolved fluorometry with the DELFIA® method," Feb. 2006, 24 pages.
SEE651 Hu 96 Tests Enzyme-linked Immunosorbent Assay Kit for Minichromosome Maintenance Deficients (MCM5); Organism Species: *Homo sapiens* (Human); Instruction manual; Jul. 2013, 8 pages.
Wollenschlaenger Dissertation, The DNA Replication Initiation Machinery as a Target for Cancer Diagnosis and Therapy, 2011, pp. 1-148.
PerkinElmer product brochure, "Unmatched sensitivity time after time" 2010, 12 pages.

\* cited by examiner

Figure 1 Sequence listing (SEQ ID NO:1)

```
         10         20         30         40         50         60
MSGFDDPGIF YSDSFGGDAQ ADEGQARKSQ LQRRFKEFLR QYRVGTDRTG FTFKYRDELK 70         80         90        100        110        120
RHYNLGEYWI EVEMEDLASF DEDLADYLYK QPAEHLQLLE EAAKEVADEV TRPRPSGEEV 130        140        150        160        170        180
LQDIQVMLKS DASPSSIRSL KSDMMSHLVK IPGIIIAASA VRAKATRISI QCRSCRNTLT 190        200        210        220        230        240
NIAMRPGLEG YALPRKCNTD QAGRPKCPLD PYFIMPDKCK CVDFQTLKLQ ELPDAVPHGE 250        260        270        280        290        300
MPRHMQLYCD RYLCDKVVPG NRVTIMGIYS IKKFGLTTSR GRDRVGVGIR SSYIRVLGIQ 310        320        330        340        350        360
VDTDGSGRSF AGAVSPQEEE EFRRLAALPN VYEVISKSIA PSIFGGTDMK KAIACLLFGG 370        380        390        400        410        420
SRKRLPDGLT RRGDINLLML GDPGTAKSQL LKFVEKCSPI GVYTSGKGSS AAGLTASVMR 430        440        450        460        470        480
DPSSRNFIME GGAMVLADGG VVCIDEFDKM REDDRVAIHE AMEQQTISIA KAGITTTLNS
```

RCSVLAAANS VFGRWDETKG EDNIDFMPTI LSRFDMIFIV KDEHNEERDV MLAKHVITLH 550        560        570        580        590        600

VSALTQTQAV EGEIDLAKLK KFIAYCRVKC GPRLSAEAAE KLKNRYIIMR SGARQHERDS 610        620        630        640        650        660

DRRSSIPITV RQLEAIVRIA EALSKMKLQP FATEADVEEA LRLFQVSTLD AALSGTLSGV 670        680        690        700        710        720

EGFTSQEDQE MLSRIEKQLK RRFAIGSQVS EHSIIKDFTK QKYPEHAIHK VLQLMLRRGE

730

IQHRMQRKVL YRLK
```

SEQ ID NO:2

Homo sapiens minichromosome maintenance complex component 5 (MCM5), mRNA
NCBI Reference Sequence: NM_006739.3 (SEQ ID NO: 2)

```
  1 ggaaaaccag aggcgcagtc atgtcgggat cgacgatcc tggcattttc tacagcgaca
 61 gcttcggggg cgacgcccag gccgacgagg ggcaggcccg caaatcgcag ctgcagaggc
121 gcttcaagga gttcctgcgg cggtaccgag tgggcaccga ccgcacgggc ttcaccttca
181 aatacaggga tgaactcaag cggcattaca acctggggga gtactggatt gaggtggaga
241 tggaggatct ggccagcttt gatgaggacc tggccgacta cttgtacaag cagccagccg
301 agcacctgca gctgctggag gaagctgcca aggaggtagc tgatgaggtg acccggcccc
361 ggccttctgg ggaggaggtg ctccaggaca tccaggtcat gctcaagtcg gacgccagcc
```

Figure 1 (cont.)

```
 421 cttccagcat tcgtagcctg aagtcggaca tgatgtcaca cctggtgaag atccctggca
 481 tcatcatcgc ggcctctgcg gtccgtgcca aggccacccg catctctatc cagtgccgca
 541 gctgccgcaa cacctcacc aacattgcca tgcgccctgg cctcgagggc tatgccctgc
 601 ccaggaagtg caacacagat caggctgggc gccccaaatg cccattggac ccgtacttca
 661 tcatgcccga caaatgcaaa tgcgtggact tccagaccct gaagctgcag gagctgcctg
 721 atgcagtccc ccacggggag atgcccagac acatgcagct ctactgcgac aggtacctgt
 781 gtgacaaggt cgtccctggg aacagggtta ccatcatggg catctactcc atcaagaagt
 841 ttggcctgac taccagcagg ggccgtgaca gggtgggcgt gggcatccga agctcctaca
 901 tccgtgtcct gggcatccag gtggacacag atggctctgg ccgcagcttt gctggggccg
 961 tgagccccca ggaggaggag gagttccgtc gcctggctgc cctcccaaat gtctatgagg
1021 tcatctccaa gagcatcgcc cctccatct tgggggcac agacatgaag aaggccattg
1081 cctgctgct ctttggggc tcccgaaaga ggctccctga tggacttact cgccgaggag
1141 acatcaacct gctgatgcta ggggaccctg gacagccaa gtcccagctt ctgaagtttg
1201 tggagaagtg ttctcccatt ggggtataca cgtctgggaa aggcagcagc gcagctggac
1261 tgacagcctc ggtgatgagg gaccttcgt cccggaattt catcatggag ggcggagcca
1321 tggtcctggc cgatggtggg gtcgtctgta ttgacgagtt tgacaagatg cgagaagatg
1381 accgtgtggc aatccacgaa gccatggagc agcagaccat ctctatcgcc aaggctggga
1441 tcaccaccac cctgaactcc cgctgctccg tcctggctgc tgccaactca gtgttcggcc
1501 gctgggatga gacgaagggg gaggacaaca ttgacttcat gcccaccatc ttgtcgcgct
1561 tcgacatgat cttcatcgtc aaggatgagc acaatgagga gagggatgtg atgctggcca
1621 agcatgtcat cactctgcac gtgagcgcac tgacacagac acaggctgtg gagggcgaga
1681 ttgacctggc caagctgaag aagtttattg cctactgccg agtgaagtgt ggccccggc
1741 tgtcagcaga ggctgcagag aaactgaaga accgctacat catcatgcgg agcggggccc
1801 gtcagcacga gagggacagt gaccgccgct ccagcatccc catcactgtg cggcagctgg
1861 aggccattgt gcgcatcgcg gaagccctca gcaagatgaa gctgcagccc ttcgccacag
1921 aggcagatgt ggaggaggcc ctgcggctct tccaagtgtc cacgttggat gctgccttgt
1981 ccggtaccct gtcaggggtg gagggcttca ccagccagga ggaccaggag atgctgagcc
2041 gcatcgagaa gcagctcaag cgccgctttg ccattggctc ccaggtgtct gagcacagca
```

Figure 1 (cont.)

```
2101 tcatcaagga cttcaccaag cagaaatacc cggagcacgc catccacaag gtgctgcagc 2161 tcatgctgcg gcgcggcgag atccagcatc gcatgcagcg caaggttctc taccgcctca 2221 agtgagtcgc gccgcctcac tggactcatg gactcgccca cgcctcgccc ctcctgccgc 2281 tgcctgccat tgacaatgtt gctgggacct ctgcctcccc actgcagccc tcgaacttcc 2341 caggcaccct cctttctgcc ccagaggaag gagctgtagt gtcctgctgc ctctgggcgc 2401 ccgcctctag cgcggttctg ggaagtgtgc ttttggcatc cgttaataat aaagccacgg 2461 tgtgttcagg taaaaaaaaa aaaaaaaaaa aaaaaaaaaa aaaaaaaaaa aaaaaaaaaa 2521 aaaaaaaaaa aaaa
```

METHODS FOR ANALYSING A URINE SAMPLE

FIELD OF THE INVENTION

The invention relates to methods for analysing urine samples, methods for aiding the diagnosis of a urological cancer in a subject, methods for detecting the presence of a biomarker indicative of a urological cancer in a subject and an apparatus for preparing cells from a urine sample.

BACKGROUND OF THE INVENTION

Urological cancers (occasionally referred to as 'urinary system cancers') are a major and increasing epidemiological problem. Two of the most economically important urological cancers are bladder cancer and prostate cancer.

Prostate cancer is the second most common cancer in men after non-melanoma skin cancer, with over 35,000 new cases diagnosed each year in the UK; about 10,200 deaths annually are caused by prostate cancer. There are around 300,000 new cases in Europe, 190,000 in the US and 670,000 worldwide annually. Cancer Research UK report that a quarter of all new cases of cancer diagnosed in men in the UK are prostate cancers and 60% of new diagnoses are in men aged over 70 years. The most common form of the disease is adenocarcinoma. The 5-year survival rate is almost 80% in the UK. There is no known environmental cause but those with close relatives with prostate or breast cancer are more at risk of developing the disease. West African and Afro-Caribbean males have an increased risk of prostate cancer.

The symptoms of prostate cancer are similar to those caused by benign enlargement of the prostate gland, and include urgency to urinate, difficulty or pain in passing urine and rarely, blood in the urine or semen. However, in many men the disease remains symptomless until painful metastases form, predominantly in the bones.

Treatment depends on the stage and grade of the tumour and the patient's general health and age. Options include active surveillance, partial or radical prostatectomy, orchidectomy, hormone treatment, and radiotherapy such as brachytherapy. Orchidectomy and hormone treatment reduce or eliminate the production of testosterone, which is essential for tumour growth.

The definite diagnosis of prostate cancer requires a multi-faceted approach. The current gold standard diagnostic test for prostate cancer is the histological examination of biopsy material. The decision to biopsy is based on age-related serum PSA level and/or an abnormal digital rectal examination (DRE). DRE, in which the gland is palpated trans-rectally to examine for abnormal morphology is also non-specific. Tumours that are too small to alter the morphology of the gland will not be detected, and abnormal morphology or enlargement is also caused by non-malignant conditions. This is a problem in the art. Samples of the prostate gland are commonly taken using TRUS (trans-rectal ultra sound)-guided needle biopsy. A number of needle cores are taken, typically up to 12, in order to maximize the area of the gland sampled. The procedure is carried out in the outpatients department under local anaesthesia by a urologist with the aid of a nurse or healthcare assistant. This procedure suffers from drawbacks including being somewhat painful for the patient, and exposing the patient to a risk of sepsis and/or bleeding. The tissue cores are microscopically examined in a laboratory for the presence of malignant cells, which has the problem of being labour intensive and requiring highly trained cytologists, as well as being vulnerable to human error.

It can be appreciated that biopsies are invasive and costly. There is a need in the art for a more cost-effective, reliable and/or non-invasive tool for the diagnosis and/or surveillance of urological cancer such as prostate cancer. Known alternate and/or less invasive diagnostic procedures for prostate cancer involve the analysis of specific biological markers ('biomarkers').

An example of a nucleic acid biomarker of prostate cancer is the PCA3 (prostate cancer gene 3) test. This urinary assay identifies non-coding mRNA from the PCA3 gene that is overexpressed in prostate cancer (Hessels & Schalken, The use of PCA3 in the diagnosis of prostate cancer. Nat Rev Urol, 6, 255-61; 2009). The PCA3 test (Gen-Probe, Inc) relies on the analysis of a first-catch urine specimen produced after a defined form of prostate massage used to express prostatic secretions, which contain epithelial cells into the urethra. As a diagnostic for prostate cancer PCA3 has a ROC value of 0.68 (Chun et al, Prostate Cancer Gene 3 (PCA3): development and internal validation of a novel biopsy nomogram. Eur Urol; 2009 vol 56 p 659-668) which is similar to that for the PSA test discussed below. However, the PCA3 test is costly and not amenable to point-of-care use, which are problems with this prior art technique.

An example of a protein biomarker, which is frequently used to indicate the presence of prostate cancer is PSA (Prostate Specific Antigen). Symptomatic patients presenting in primary care are typically given a serum PSA test and a DRE. However, PSA is not specific for prostate cancer. PSA is a constitutively expressed tissue specific intracellular enzyme. A low concentration of PSA is present in the serum of men with healthy prostate glands. A raised level of PSA in serum occurs due to leakage from the prostate gland and is an indication of the relative size of the gland. Raised PSA can occur in non-malignant conditions such as benign prostatic hyperplasia and prostatitis and also in prostate cancer. As men grow older, the volume of the gland increases resulting in rising PSA levels in the absence of malignant disease. In a recent study it was found that 60-70% of 'positive' PSA tests (serum level of PSA greater than 4 ng/mL) were not associated with cancer (Kilpeläinen et al., False-positive screening results in the Finnish prostate cancer screening trial, British Journal of Cancer. 102, 469-474; 2010). The high rate of false positive results leads to many unnecessary biopsy operations and renders the test inappropriate for population screening. In addition the PSA test fails to detect a significant number of cases of prostate cancer, particularly in younger men. The accuracy of the PSA test as measured in ROC (receiver operating characteristic) analysis is 0.678 (Thompson et al., Operating characteristics of a prostate-specific antigen in men with an initial PSA level of 3.0 ng/ml or lower. JAMA, 294, 66-70; 2005). In the UK, PSA tests are usually carried out in hospital laboratories although rapid point-of-care assays are available.

Bladder cancer is the fourth most common cancer in men and the ninth most common cancer in women and results in significant morbidity and mortality (Jemal et al. CA Cancer J Clin. 2007. 57:43-66.). Most patients with bladder cancer receive the diagnosis after they present with gross or microscopic haematuria or with other irritative voiding symptoms, such as frequency and dysuria. At initial diagnosis, approximately 70% of patients have bladder cancers that are confined to the epithelium or subepithelial connective tissue. These cancers can be managed with endoscopic resection and intravesical therapy. The recurrence rate for these tumours ranges from 50% to 70% and 10% to 15% of cases progress to muscle invasion over a 5-year period (Shariat et al., 2008. Rev Urol. 10:120-135). Recurrence may be seen locally and more rarely in the upper urinary tract even after several years, necessitating lifelong surveillance. The remaining 30% of patients have muscle-invasive cancer at initial diagnosis. Of this population, 50% have distant metastasis within 2 years, and 60% die within 5 years despite treatment.

The definite diagnosis of bladder cancer requires a combination of procedures. Presently there are no methods to identify accurately and easily the presence of early bladder cancer. Screening for bladder cancer in patients who present to the urology clinic with appropriate symptoms is currently done with urinalysis, cystoscopy and a scanning procedure such as abdominal ultrasound, intravenous urogram, computed tomography or magnetic resonance imaging. Urine cytology, in which cells from urine samples are examined microscopically, is used occasionally. Cystoscopy, the mainstay for the detection of bladder cancer, is a relatively short, minimally traumatic procedure performed with local urethral anaesthesia, which identifies nearly all papillary and sessile lesions. Nevertheless, it is still invasive and a cause of discomfort and distress to the patient. In addition, cystoscopy may be inconclusive at times because of the grossly abnormal appearance of the bladder mucosa, especially in patients with an indwelling catheter or active inflammation, and it is unable to detect cancers within the ureters. Although considered the gold standard for diagnosis of bladder cancer because it allows direct visualization and biopsy of the bladder urothelium, cystoscopy has an appreciable false-negative rate either from operator error or from small areas of "carcinoma in situ", which may be difficult to detect. (van der Poel & Debruyne. Curr Opin Urol. 2001; 11:503-509; Herr. BJU Int. 1999; 84:1102-1103.)

In urine cytology for bladder cancer, exfoliated cells can be investigated for the presence of specific cell-surface antigens, nuclear morphology, gene expression or other biological markers. Urine cytology has a high sensitivity and specificity for the detection of high-grade bladder cancer, but it lacks the sensitivity to detect low grade tumours (Wiener et al. Acta Cytol. 1993; 37:163-169). The accuracy of urine cytology in predicting bladder cancer recurrence may vary widely, in part because there is an element of subjectivity in the interpretation of the results. Hence, cytology is not ideal for screening for and surveillance of bladder cancer.

Mcm5 is a biomarker for cancer (WO99021014). In a non-invasive study of bladder cancer it was demonstrated that the results of immunofluorometric detection of minichromosome maintenance complex component 5 (Mcm5) in urine combined with results from ELISA detection of urinary NMP22 (nuclear matrix protein 22), allowed nearly all life threatening disease to be identified (Kelly et al., Bladder Cancer Diagnosis and Identification of Clinically Significant Disease by Combined Urinary Detection of Mcm5 and Nuclear Matrix Protein 22 PlosONE. 7, e40305; 2012).

A raised level of Mcm proteins such as Mcm5 in urine sediment is associated with malignant changes in the prostate gland. Hence raised levels of these Mcm proteins could be used to detect prostate cancer. Using DELFIA® (Dissociation-Enhanced Lanthanide Fluorometric Immunoassay) and anti-Mcm5 monoclonal antibodies in a double antibody assay, Dudderidge et al. (BJC, 103, 701-707; 2010) investigated the use of Mcm5 as a urinary biomarker for prostate cancer detection and concluded that it 'seems to be a simple, accurate and non-invasive method for identifying patients with prostate cancer'. Compared with the PSA test, which has a specificity of 30%, the specificity of Mcm5 was estimated at between 73% and 93%. Importantly, benign prostatic hyperplasia did not generate false positive results, which is a disadvantage of the PSA test. The assessment of Mcm5 and other Mcm proteins currently requires a specialised laboratory with sophisticated instrumentation and highly skilled operatives, thus the assay is not suited to the pathology laboratory or point-of-care applications.

This is further compounded by the complicated methods which are used to prepare samples for analysis by detection of biomarkers. Since Mcm proteins are present in cells, the Mcm proteins must be released from cells in a sample such as a urine sample. A method for preparing such samples is disclosed in, Dudderidge et al. (BJC, 103, 701-707; 2010) which describes that the samples must be processed using a large number of steps including (1) centrifugation at 1500 g for 5 min at 4° C., (2) discarding the supernatant, (3) washing the cell pellet three times with 500 µl of PBS, (3) resuspending the cell pellets in 250 µl or 500 µl of processing buffer (PBS, 0.4% sodium dodecyl sulphate and 0.02% sodiumqzide), (4) incubating the resuspended samples at 95° C. for 45 minutes, (5) shearing the DNA in the sample by passing the lysis through a 21-gauge needle, (6) digestion of the nucleic acids with DNase I and RNase A for 2 h at 37° C., and (7) centrifugation at 15000 g for 10 min. This method is also seen in other documents such as Stoeber et al 2002 (Journal of the National Cancer Institute, 94, 1071-1079; 2002). This urine sample preparing method involves multiple steps using multiple reagents and is extremely time-consuming. Typically these methods take at least two hours. Thus, there is a need for a method and/or apparatus to prepare urine samples which is considerably less onerous. Such a method would be more suited to pathology laboratory or point-of-care applications.

The present assays for detection of Mcm proteins, particularly Mcm5, require the use of DELFIA technology which is complicated to use and involves expensive equipment and reagents. Thus, an assay based on DELFIA is not suitable for pathology laboratory or point-of-care applications and there is a need for an assay that is suitable for such applications.

SUMMARY OF THE INVENTION

The present invention provides methods, compositions and kits useful for the early detection of urological cancer such as prostate cancer without the need for invasive surgical procedures. The methods and compositions are suitable for use in the clinical laboratory and/or for point-of-care applications.

The present inventors have demonstrated that the complicated urine sample preparation methods described in the prior art are not required to release biomarkers such as Mcm5 from cells in samples such as urine samples. Rather, all that is required is to expose the sample to a lysis buffer which is capable of releasing the biomarker from cells in the sample. This is much simpler than the prior art methods. According to the present invention, in some embodiments the cells in a sample (such as a urine sample) may be prepared and lysed by the addition of a single lysate buffer. Similarly the inventors have designed an apparatus that can be used to readily perform this exposure to lysis buffer.

The present inventors have also demonstrated that an Mcm protein assay which does not use immunofluorescence can accurately detect whether a subject has a urological cancer. This is beneficial over prior art techniques which use Europium labels and DELFIA detection. Such methods are expensive and complicated and thus unsuitable for use in pathology laboratory or point-of-care applications.

Accordingly in a first aspect there is provided a method for analysing a urine sample from a subject comprising
 a. exposing the urine sample to a lysis buffer wherein the lysis buffer is capable of releasing at least one biomarker from cells in the urine sample; and
 b. performing an assay to determine the concentration of the at least one biomarker in the urine sample.

In a second aspect there is provided a method for analysing a urine sample from a subject comprising a step of exposing the urine sample to a lysis buffer wherein:
 a. the lysis buffer is not PBS containing 0.4% sodium deoxycholate and 0.02% sodium azide;
 b. the method does not comprise incubation of the urine sample at a temperature greater than 90° C. for around 45 minutes;
 c. the method does not comprise shearing the nucleic acids by passing the urine sample through a 21 gauge needle;
 d. the method does not comprise digesting the nucleic acids by exposing the urine sample to DNase I or RNase A; and/or
 e. the method does not comprise centrifuging the sample at 15,000 g for ten minutes;
and wherein the method further comprises a step of performing an assay to determine the concentration of at least one biomarker in the urine sample.

In a third aspect there is provided a method for analysing a urine sample comprising cells from a subject wherein the urine sample is prepared using a process consisting of the following steps:
 a. concentrating the cells in the urine sample; and
 b. exposing the concentrated cells to lysis buffer;
and wherein the method further comprises a step of performing an assay to determine the concentration of at least one biomarker in the urine sample.

In a fourth aspect there is provided a method for analysing a urine sample comprising cells from a subject wherein the urine sample is prepared using a process consisting of the following steps:
 a. centrifugation of the sample to provide a sample pellet; and
 b. resuspension of the pelleted cells from the sample in a lysis buffer;
and wherein the method further comprises a step of performing an assay to determine the concentration of at least one biomarker in the urine sample.

In a fifth aspect there is provided a kit comprising a lysis buffer which is capable of releasing at least one biomarker from cells in a urine sample, a capture antibody and a detection antibody, wherein the capture antibody and the detection antibody bind to Mcm5.

In a sixth aspect there is provided an apparatus for preparing cells from a urine sample, the apparatus comprising:
 an inlet;
 a first valve arrangement positioned downstream of the inlet and in fluid communication with the inlet;
 a filter for capturing cells from urine, the filter arranged downstream of the first valve arrangement and in fluid communication with the first valve arrangement;
 a second valve arrangement positioned downstream of the filter and in fluid communication with the filter;
 an outlet arranged downstream of the second valve arrangement and in fluid communication with the second valve arrangement;
 a first buffer reservoir for holding a lysis buffer, the first buffer reservoir being in fluid communication with the first valve arrangement;
 a second buffer reservoir for holding a lysis buffer, the second buffer reservoir being in fluid communication with the second valve arrangement;
 wherein the first and second valve arrangements can be configured such that:
 in a first configuration of the first and second valve arrangements, fluid communication between the first buffer reservoir and the filter is blocked, fluid communication between the second buffer reservoir and the filter is blocked, and fluid communication between the inlet, filter and outlet is open, such that urine is able to flow from the inlet to the outlet via the filter; and
 in a second configuration of the first and second valve arrangements, fluid communication between the first buffer reservoir and the filter is open, fluid communication between the second buffer reservoir and the filter is open and flow through the inlet and out the outlet is blocked, such that lysis buffer is able to flow between the first buffer reservoir and the second buffer reservoir via the filter.

In a seventh aspect there is provided a method for preparing cells from a urine sample, the method comprising:
 passing the urine sample through a filter for capturing cells, such that cells are captured in the filter;
 passing a lysis buffer through the filter, such that the captured cells are exposed to the lysis buffer;
 incubating the filter for a period of time, such that the lysis buffer causes the cells to release at least one biomarker.

In an eighth aspect there is provided a method for detecting the presence of a biomarker indicative of a urological cancer in a subject, the method comprising:
 a. performing an assay on a sample from a subject to determine the concentration of an Mcm protein;
 b. comparing the concentration of the Mcm protein determined in step a. to reference values;
wherein the assay is not an immunofluorometric assay.

In a ninth aspect there is provided a kit suitable for performing the methods of the invention.

In a tenth aspect there is provided a kit for use in the diagnosis of urological cancer comprising a capture antibody and a detection antibody wherein (a) the capture antibody and the detection antibody bind specifically to Mcm5, (b) the capture antibody is bound to a solid support, and (c) the detection antibody is conjugated to horseradish peroxidase.

In an eleventh aspect there is provided a device for analysing a urine sample from a subject, the device comprising:
 the apparatus of the invention; and
 an assay device capable of determining the concentration of the at least one biomarker in the urine sample.

In a twelfth aspect there is provided a use of lysis buffer of the invention for releasing at least one biomarker from cells in a urine sample.

BRIEF DESCRIPTION OF THE DRAWINGS

FIG. 1 is a sequence listing.

DETAILED DESCRIPTION

Definitions

Figure 2:
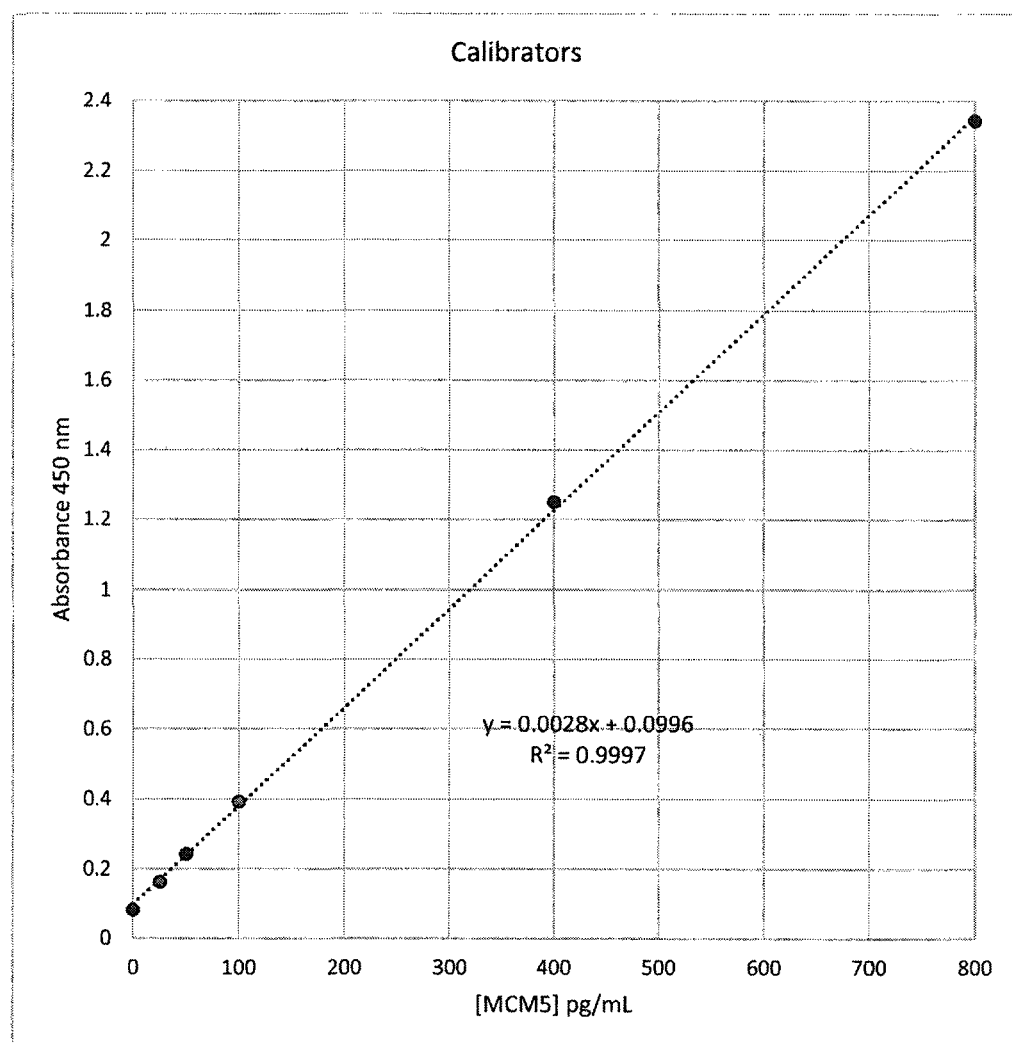
FIG. 2 shows a graph describing the absorbance at 450 nm of different concentrations of Mcm5.

The term 'comprises' (comprise, comprising) should be understood to have its normal meaning in the art, i.e. that the stated feature or group of features is included, but that the term does not exclude any other stated feature or group of features from also being present.

The term "consists of" should also be understood to have its normal meaning in the art, i.e. that the stated feature or group of features is included, to the exclusion of further features. For example a lysis buffer consisting of a detergent contains detergent and no other components. On the other hand a lysis buffer comprising a detergent consisting of polysorbate 80 may comprise components other than detergents but the only detergent in the lysis buffer is polysorbate 80.

For every embodiment in which "comprises" or "comprising" is used, we anticipate a further embodiment in which "consists of" or "consisting of" is used. Thus, every disclosure of "comprises" should be considered to be a disclosure of "consists of".

Urine Sample Preparation Methods

The present invention relates to methods for analysing urine samples comprising exposing the urine sample to a lysis buffer. These methods are considerably simpler and more cost effective than prior art methods.

The term 'exposing the urine sample to a lysis buffer' can be considered to refer to manipulating the urine sample in such a way that the cells within the urine sample (or a substantial portion of these cells) are in contact with the lysis buffer. Suitably, the urine sample is centrifuged to provide a sample pellet, the supernatant is discarded and the sample pellet is re-suspended in the lysis buffer. Alternatively, for example, concentrated buffer components are added to a liquid urine sample to form a solution comprising the urine sample exposed to the lysis buffer.

In one embodiment the urine sample is prepared using a process consisting of the following steps:
 a. concentrating the cells in the urine sample; and
 b. exposing the concentrated cells to lysis buffer.

Suitably step a. of concentrating the cells in the urine sample is performed by filtering the urine sample to capture cells. Suitably steps a. of concentrating the cells in the lysis buffer and b. of exposing the concentrated cells to lysis buffer are carried out using a device or apparatus of the invention or using the method for preparing cells from a urine sample of the invention.

In a further preferred embodiment the method comprises a step of concentrating cells in the urine sample prior to the step of exposing the urine sample to a lysis buffer, exposing the concentrated cells to lysis buffer or resuspension of the pelleted cells from the sample in lysis buffer.

In one embodiment the urine sample comprising cells is prepared using a process consisting of the following steps:
a. centrifugation of the sample to provide a sample pellet; and b. resuspension of the pelleted cells from the sample in a lysis buffer.

Suitably the sample is centrifuged for between 1 minute and 30 minutes at between 500 g and 5000 g, for between 1 minute and 20 minutes at between 750 g and 2500 g, for between 3 minutes and 10 minutes at between 750 g and 2000 g, or for around 5 minutes at 1500 g.

Suitably the pellet is resuspended using an adjustable pipette with a disposable tip.

In one embodiment the method does not comprise incubation of the urine sample at a temperature greater than 90° C. for around 45 minutes. Optionally the method does not comprise incubation of the urine sample at a high temperature. In one embodiment the high temperature is a temperature greater than 50° C., greater than 60° C., greater than 70° C., greater than 80° C., greater than 90° C., between 50° C. and 120° C., between 60° C. and 110° C., between 70° C. and 100° C., or between 80° C. and 100° C. Optionally the method does not comprise incubation of the urine sample at a high temperature for more than 30 minutes, more than 35 minutes, more than 40 minutes, more than 45 minutes, between 30 minutes and 2 hours, between 35 minutes and 2 hours, or between 40 minutes and 2 hours.

In a further embodiment the method does not comprise shearing the nucleic acids by passing the urine sample through a 21 gauge needle. In a further embodiment the method does not comprise exposing the urine sample to mechanical shearing.

In a further embodiment the method does not comprise digesting the nucleic acids by exposing the urine sample to DNase I or RNase A.

Optionally the method does not comprise incubation of the urine sample at a temperature greater than 90° C. for greater than 45 minutes, shearing nucleic acids in the urine sample by passing the urine sample through a 21 gauge needle, digesting the nucleic acids by exposing the urine sample to DNase I or RNase A, centrifuging the sample at 15,000 g for 10 minutes, wherein the lysis buffer is not PBS containing 0.4% sodium deoxycholate and 0.02% sodium azide.

The phrase 'does not comprise digesting the nucleic acids by exposing the urine sample to DNase I or RNase A' is means the sample should not be exposed to a concentration of DNase I or RNase A that is effective to cause significant digestion of the nucleic acids in the sample. Preferably the sample is not exposed to more than 20 U/ml DNase I or more than 1 µg/mL RNase A. Suitably the sample is not exposed to more than 1 U/ml, more than 5 U/ml, more than 10 U/ml, more than 15 U/ml, between 1 U/ml and 500 U/ml, between 5 U/ml and 250 U/ml, between 10 U/ml and 100 U/mL or between 15 U/ml and 100 U/ml of DNase I. Suitably the sample is not exposed to more than 0.1 µg/mL, more than 0.2 µg/mL, more than 0.5 µg/mL, more than 0.7 µg/mL, between 0.1 µg/ml and 100 µg/ml, between 0.5 µg/mL and 50 µg/mL or between 0.5 µg/mL and 25 µg/mL of RNase A.

In a further embodiment the method does not comprise centrifuging the sample at 15,000 g for ten minutes. In a further embodiment the method does not comprise centrifuging the sample. In a further embodiment the method does not comprise centrifuging the sample at more than 10,000 g, more than 12,000 g, more than 14,000 g or more than 14,500 g. In a further embodiment the method does not comprise centrifuging the sample for more than 2 minutes, more than 5 minutes, more than 7 minutes or more than 8 minutes.

In a preferred embodiment the method is a method for releasing at least one biomarker such as Mcm5 from cells in the urine sample and determining the concentration of the at least one biomarker released from the cells.

In one embodiment the methods for analysing a urine sample of the invention are part of a larger method for aiding the diagnosis of a urological cancer in a subject.

Lysis Buffers of the Invention

Lysis buffers are generally buffers which are used for the purpose of lysing cells. In addition to releasing one or more biomarkers from cells, the lysis buffer must be compatible with the method used for subsequent analysis. For example, where the analysis method is double-antibody sandwich ELISA, the lysis buffer must not degrade the capture antibody bound to the surface of the microtitre plate. Lysis buffers generally but not exclusively comprise one or more detergents (also known as surfactants), one or more salts and a buffering agent. The concentrations of these components affect the efficacy of the lysis buffer.

In a preferred embodiment of the invention the lysis buffer is capable of releasing a biomarker such as Mcm5 from cells in the sample. A lysis buffer will be considered to be "capable of releasing a biomarker such as Mcm5 from cells in the sample" if the amount of the biomarker (such as Mcm5) released is greater than 40%, 50%, 60%, 70%, or 80% the amount released when a buffer containing 0.08% sodium deoxycholate, 0.08% CHAPS, 2 mM EDTA, 150 mM TRIZMA® pH 7.6 is used. In an embodiment a lysis buffer will be considered to be "capable of releasing a biomarker such as Mcm5 from cells in the sample" if the amount of the biomarker such as Mcm5 released is greater than 40%, 50%, 60%, 70%, or 80% the amount released when a buffer containing 10 mM Tris (pH 7.6), 200 mM NaCl, 2.5% BSA, 0.1% TRITON™ X-100 and 0.09% Sodium azide is used. The amount of the biomarker such as Mcm5 that is released using a lysis buffer may be determined by assaying the amount present after exposure to the lysis buffer and comparing it to a reference sample (preferably a sample which is substantially the same or identical to the first sample) which has been exposed to a buffer containing 0.08% sodium deoxycholate, 0.08% CHAPS, 2 mM EDTA, 150 mM TRIZMA® pH 7.6. In an embodiment the amount of a biomarker such as Mcm5 that is released using a lysis buffer may be determined by assaying the amount present after exposure to the lysis buffer and comparing it to a reference sample (preferably a sample which is substantially the same or identical to the first sample) which has been exposed to a buffer containing 10 mM Tris (pH 7.6), 200 mM NaCl, 2.5% BSA, 0.1% TRITON™ X-100 and 0.09% Sodium azide. The amount of a biomarker such as Mcm5 that is released may be measured using a sandwich ELISA assay such as the assay described in Example 1. The antibodies used in the sandwich assay should be antibodies that bind to the biomarker such as Mcm5, for example a first monoclonal antibody or second monoclonal antibody according to the invention. Preferably 12A7 and 4B4 antibodies are used.

In an even more preferred embodiment of the invention the lysis buffer is capable of releasing Mcm5 from cells in the urine sample and does not substantially degrade the Mcm5 protein. A buffer can be considered to not substantially degrade Mcm5 protein if the amount of intact Mcm5 present after exposure of the sample to the lysis buffer is greater than 40%, 50%, 60%, 70%, or 80% the amount of intact Mcm5 after exposure to a buffer containing 0.08% sodium deoxycholate, 0.08% CHAPS, 2 mM EDTA, 150 mM TRIZMA® pH 7.6. Mcm5 protein can be considered to be intact, if the binding site for antibodies that bind to SEQ ID NO: 1 and SEQ ID NO: 2 (such as the first monoclonal antibody and second monoclonal antibody or antibodies 12A7 and 4B4) are present. It is within the capabilities of the skilled person to determine how much Mcm5 within a sample is degraded. The sample should be tested to see whether the Mcm5 within the sample can bind to the first monoclonal antibody and the second monoclonal antibody according to the invention. This may be measured using a sandwich ELISA assay such as that described in Example 1. The antibodies used in the sandwich assay should be antibodies that bind to Mcm5, for example a first monoclonal antibody or second monoclonal antibody of the invention. Preferably 12A7 and 4B4 antibodies are used.

A lysis buffer can be considered to not denature an antibody if the activity of the antibody after exposure to the lysis buffer is 40%, 50%, 60%, 70% or 80% the activity of the antibody prior to exposure to the lysis buffer. The activity of the antibody may be tested using an ELISA assay such as that described in Example 1.

In one embodiment the lysis buffer is capable of releasing Mcm5 from cells in a fresh sample. The term "fresh sample" refers to a sample that has not been frozen. Preferably, the "fresh sample" has been obtained from a patient less than 10 days, less than 5 days, less than 2 days or less than 1 day prior to its use in the methods of the invention. In one embodiment the cells are exposed to the lysis buffer and then frozen before further treatment. For example, the urine sample may be concentrated by centrifugation followed by discarding the supernatant and then the lysis buffer may be added to the concentrated cells. Preferably the frozen sample is thawed prior to a step of performing an assay to determine the concentration of the at least one biomarker in the urine sample. Preferably the sample is frozen for at least 1 hour, at least 1 day, at least 5 days or at least 10 days prior to a step of performing an assay to determine the concentration of the at least one biomarker in the urine sample. Preferably the sample is frozen for between 1 hour and 1 year, between 1 hour and 6 months, between 1 day and 3 months or around one week prior to a step of performing an assay to determine the concentration of the at least one biomarker in the urine sample.

In an embodiment of the invention the lysis buffer is CYTOBUSTER™ Protein Extraction Reagent.

In one embodiment the lysis buffer is not PBS containing 0.4% sodium deoxycholate and 0.02% sodium azide.

In one embodiment the lysis buffer comprises a detergent (also referred to as a surfactant). In general detergents are compounds that are known to disrupt cell walls. Detergents are amphiphilic having both hydrophobic and hydrophilic regions. Suitable detergents are well known to the person of skill in the art. Suitably the detergent is an anionic detergent, a cationic detergent, a non-ionic detergent or a zwitterionic detergent. Suitably the detergent is selected from the group consisting of sodium deoxycholate, 3-[(3-Cholamidopropyl) dimethylammonio]-1-propanesulphonate (CHAPS), alkylbenzenesulphonates, sodium dodecylbenzenesulphonate, a Tween detergent (such as polyoxyethylene (20) sorbitan monooleate or TWEEN® 20 (polyoxyethylene (20) sorbitan monolaurate)), and a TRITON™ detergent (such as polyethylene glycol p-(1,1,3,3,-tetramethylbutyl)-phenyl ether or TRITON™ X-100). Suitably the detergent comprises sodium deoxychlolate. Suitably the detergent comprises CHAPS. Suitably the detergent comprises sodium deoxycholate and CHAPS. Suitably the lysis buffer comprises sodium deoxycholate at a concentration between 0.01% and 0.15%, between 0.03% and 0.10%, between 0.05% and 0.09%, or about 0.08%. Suitably the lysis buffer comprises CHAPS at a concentration between 0.01% and 0.15%, between 0.03% and 0.10%, between 0.05% and 0.09%, or about 0.08%. Suitably the detergent comprises TRITON™ X-100. Preferably the detergent comprises TRITON™ X-100 at a concentration between 0.01% and 25%, between 0.01% and 10%, between 0.05% and 5%, between 0.05% and 1%, between 0.05% and 0.5%, between 0.075% and 0.125% or around 0.1%. Suitably the detergent consists of TRITON™ X-100. Preferably the detergent consists of TRITON™ X-100 at a concentration between 0.01% and 25%, between 0.01% and 10%, between 0.05% and 5%, between 0.05% and 1%, between 0.05% and 0.5%, between 0.075% and 0.125% or around 0.1%. Suitably the detergent comprises a polysorbate, preferably polysorbate 20 (also known as TWEEN® 20). Suitably the detergent comprises polysorbate at a concentration between 0.01% and 5%, between 0.02% and 1%, between 0.03% and 0.07% or around 0.05%. Suitably the detergent comprises sodium deoxycholate or sodium dodecylsulphate. For example the detergent may comprise sodium deoxycholate or sodium dodecylsulphate at a concentration between 0.1% and 20%, between 0.5% and 10%, between 0.5% and 5%, between 0.75% and 1.25% or around 1%.

In a further embodiment the lysis buffer comprises a chelating agent. In a further embodiment the lysis buffer does not comprise a chelating agent. Chelating agents are multidentate ligands which can coordinate metal ions. Suitably the chelating agent is EDTA (ethylenediaminetetraacetic acid). Optionally the lysis buffer comprises EDTA at a concentration between 0.5 mM and 10 mM, between 1 mM and 5 mM, between 1.5 mM and 3 mM, or about 2 mM.

In a further embodiment the lysis buffer comprises a buffer component. A buffer component can be considered to be any component which maintains the pH of the lysis buffer at a pH varying by less than 2.0 pH units, 1.5 pH units or 1.0 pH units. Examples of buffers which are suitable for this purpose are well known to the person skilled in the art. In an embodiment the buffer component is a buffer selected from the group consisting of TAPS (3-{[tris(hydroxymethyl) methyl]amino}propanesulphonic acid), Bicine (N,N-bis(2-hydroxyethyl)glycine), Tris (tris(hydroxymethyl)methylamine), Tricine (N-tris(hydroxymethyl(methylglycine), TAPSO (3-[N-Tris(hydroxymethyl)methylamino]-2-hydroxypropanesulphonic acid, HEPES (4-2-hydroxyethyl-1-piperazineethanesulphonic acid) and MOPS (3-(N-morpholino)propanesulphonic acid. Suitably the buffer component comprises Tris, phosphate buffered saline (PBS), MOPS, bicarbonate or HEPES buffer. Suitably the buffer component comprises Tris, PBS, MOPS or bicarbonate buffer. Suitably the buffer component comprises Tris, PBS or bicarbonate buffer. In one embodiment the buffer component is Tris or TRIZMA® buffer. In one embodiment the buffer component comprises or consists of Tris or TRIZMA® buffer. Trizma may refer to TRIZMA® Pre-set crystals pH 7.6' (Sigma-Aldrich Cat. No. T7943). In a further embodiment the buffer component maintains the pH of the buffer at a pH between pH 4 and pH 9, between pH 5 and pH 8, between pH 6 and pH 8, or around pH 7.6. Optionally the buffer component is Tris or TRIZMA® buffer, and the buffer component maintains the pH of the lysis buffer between pH 4 and pH 9, between pH 5 and pH 8, between pH 6 and pH 8, or around pH 7.6. Optionally the buffer component comprises or consists of Tris or TRIZMA® buffer, and the buffer component maintains the pH of the lysis buffer between pH 4 and pH 9, between pH 5 and pH 8, between pH 6 and pH 8, or around pH 7.6.

Preferably the buffer component comprises tris buffer, for example at a concentration greater than 5 mM, between 5 mM and 350 mM, between 200 mM and 300 mM, between 225 mM and 275 mM, between 10 mM and 25 mM, between 8 mM and 12 mM, around 10 mM or around 250 mM. Preferably the buffer component consists of tris buffer, for example at a concentration greater than 5 mM, between 5 mM and 350 mM, between 200 mM and 300 mM, between 225 mM and 275 mM, between 10 mM and 25 mM, between 8 mM and 12 mM, around 10 mM or around 250 mM. Suitably the buffer component comprises phosphate buffered saline, for example at a concentration of between 5 mM and 250 mM, between 50 mM and 250 mM or around 100 mM.

In an embodiment the lysis buffer comprises sodium deoxycholate at a concentration between 0.01% and 0.15%, CHAPS at a concentration between 0.01% and 0.15%, EDTA at a concentration between 0.5 mM and 10 Mm, and Tris or TRIZMA® buffer, wherein the Tris or TRIZMA® buffer maintains the pH of the lysis buffer between pH 4 and pH 9. In a further embodiment the lysis buffer comprises sodium deoxycholate at a concentration between 0.05% and 0.09%, CHAPS at a concentration between 0.05% and 0.09%, EDTA at a concentration between 1.5 mM and 3 mM, and Tris or TRIZMA® buffer, wherein the Tris or TRIZMA® buffer maintains the pH of the lysis buffer between pH 6 and pH 8. In a further embodiment the lysis buffer comprises sodium deoxycholate at a concentration about 0.08%, CHAPS at a concentration about 0.08%, EDTA at a concentration about 2 mM, and Tris or TRIZMA® buffer, wherein the Tris or TRIZMA® buffer maintains the pH of the lysis buffer around pH 7.6.

In one embodiment the lysis buffer comprises a salt selected from the group consisting of sodium chloride, potassium chloride, magnesium chloride, sodium sulphate, potassium sulphate, magnesium sulphate, sodium acetate, potassium acetate, magnesium acetate, sodium phosphate, potassium phosphate or magnesium phosphate. Preferably the salt is a sodium salt or a potassium salt. Suitably the salt is sodium chloride or potassium chloride. Suitably the salt is at a concentration between 20 mM and 300 mM, between 150 mM and 300 mM, between 100 mM and 200 mM, between 150 mM and 250 mM, between 175 mM and 275 mM or around 200 mM. Suitably the salt comprises or consists of sodium chloride or potassium chloride. Suitably the salt is at a concentration between 20 mM and 300 mM, between 150 mM and 300 mM, between 100 mM and 200 mM, between 150 mM and 250 mM, between 175 mM and 275 mM or around 200 mM. Preferably the salt is sodium chloride, for example at a concentration between 20 mM and 300 mM, between 150 mM and 300 mM, between 100 mM and 200 mM or around 200 mM. Preferably the salt comprises or consists of sodium chloride, for example at a concentration between 20 mM and 300 mM, between 150 mM and 300 mM, between 100 mM and 200 mM or around 200 mM.

In one embodiment the lysis buffer has an ionic strength of between 1 mM and 500 mM, between 50 mM and 450 mM, between 100 mM and 250 mM, between 100 mM and 175 mM, or between 125 mM and 175 mM. Various components of the buffer may contribute to this ionic strength. For example, the lysis buffer may comprise a buffer component (such as Tris) and an additional salt component (such as sodium chloride) and both of these components may contribute to the ionic strength of the lysis buffer.

In one embodiment the lysis buffer comprises a stabiliser. A "stabiliser" is a component that reduces the breakdown of proteins. For example, a stabiliser reduces the breakdown of Mcm5. Whether a buffer component stabilises Mcm5 can be tested using a sandwich ELISA assay such as the assay described in Example 1. For example, a sample may be exposed to a lysis buffer comprising the potential stabiliser and a control sample may be exposed to a lysis buffer lacking the potential stabiliser. The level of Mcm5 that can be detected after exposure is measured using the sandwich ELISA. If the level of Mcm5 in the sample having the buffer comprising the potential stabiliser is greater than the level of Mcm5 in the sample having the buffer that does not comprise the potential stabiliser, then the potential stabiliser is a stabiliser according to the present invention. A stabiliser of the invention may prevent the breakdown of Mcm5 such that 1%, 2%, 5%, 10%, 20% or 25% more Mcm5 is present after storage in a buffer comprising a stabiliser for 1 day, 3 days, 5 days, 1 week or 2 weeks (compared to a buffer that does not comprise the stabiliser).

The stabiliser may be a stabiliser selected from the group consisting of bovine serum albumin (BSA), foetal bovine serum (FBS) and a protease inhibitor. For example, protease inhibitors include 4-(2-aminoethyl)benzenesulphonyl fluoride hydrochloride (PEFABLOC® SC or AEBSF), a protease inhibitor cocktail (such as Sigma P8340) comprising AEBSF, aprotinin, bestatin hydrochloride, N-(trans-epoxysuccinyl)-L-leucine 4-guanidinobutylamide (E-64), leupeptin hemisulphate salt and pepstatin A, and Roche COMPLETE™ protease inhibitor. Preferably the stabiliser is BSA, for example at a concentration between 0.1% and 20%, between 0.1% and 10%, between 0.1% and 5%, between 1% and 3%, between 2.2% and 2.7% or around 2.5%. Preferably the stabiliser comprises or consists of BSA, for example at a concentration between 0.1% and 20%, between 0.1% and 10%, between 0.1% and 5%, between 1% and 3%, between 2.2% and 2.7% or around 2.5%.

The lysis buffer may comprise an antimicrobial agent. A component is an "antimicrobial agent" if it reduces the replication of microbes, for example bacteria, viruses or fungi. In one embodiment the antimicrobial agent is sodium azide or an isothiazolone. In one embodiment the antimicrobial agent comprises or consists of sodium azide or an isothiazolone. The isothiazolone may be 2-methyl-4-isothiazolin-3-one and/or 5-chloro-2-methyl-4-isothiazolin-3-one. Preferably the antimicrobial agent comprises sodium azide, for example at a concentration between 0.01% and 5%, between 0.02% and 1.5%, between 0.07% and 0.12% or around 0.09%. Preferably the antimicrobial agent consists of sodium azide, for example at a concentration between 0.01% and 5%, between 0.02% and 1.5%, between 0.07% and 0.12% or around 0.09%.

The lysis buffer may comprise:
(i) between 1 mM and 500 mM Tris;
(ii) between 5 mM and 500 mM sodium chloride;
(iii) between 0.1% and 20% BSA;
(iv) between 0.001% and 10% TRITON™ X-100; and
(v) between 0.001% and 1% sodium azide.

The lysis buffer may consists of:
(i) between 1 mM and 500 mM Tris;
(ii) between 5 mM and 500 mM sodium chloride;
(iii) between 0.1% and 20% BSA;
(iv) between 0.001% and 10% TRITON™ X-100; and
(v) between 0.001% and 1% sodium azide.

Alternatively, the lysis buffer may comprise:
(i) between 1 mM and 150 mM Tris;
(ii) between 50 mM and 400 mM sodium chloride;
(iii) between 0.5% and 10% BSA;
(iv) between 0.01% and 5% TRITON™ X-100; and
(v) between 0.01% and 0.5% sodium azide.

Alternatively, the lysis buffer may consist of:
(i) between 1 mM and 150 mM Tris;
(ii) between 50 mM and 400 mM sodium chloride;
(iii) between 0.5% and 10% BSA;
(iv) between 0.01% and 5% TRITON™ X-100; and
(v) between 0.01% and 0.5% sodium azide.

Alternatively, the lysis buffer may comprise:
(i) between 1 mM and 100 mM Tris;
(ii) between 100 mM and 300 mM sodium chloride;
(iii) between 1% and 5% BSA;
(iv) between 0.01% and 1% TRITON™ X-100; and
(v) between 0.01% and 0.1% sodium azide.

Alternatively, the lysis buffer may consist of:
(i) between 1 mM and 100 mM Tris;
(ii) between 100 mM and 300 mM sodium chloride;
(iii) between 1% and 5% BSA;
(iv) between 0.01% and 1% TRITON™ X-100; and
(v) between 0.01% and 0.1% sodium azide.

The lysis buffer may comprise:
(i) around 10 mM Tris;
(ii) around 200 mM sodium chloride;
(iii) around 2.5% BSA;
(iv) around 0.1% TRITON™ X-100; and
(v) around 0.09% sodium azide.

The lysis buffer may consist of:
(i) around 10 mM Tris;
(ii) around 200 mM sodium chloride;
(iii) around 2.5% BSA;
(iv) around 0.1% TRITON™ X-100; and
(v) around 0.09% sodium azide.

The lysis buffer may be RIPA buffer.

In one embodiment the lysis buffer of the invention is used for releasing at least one biomarker from cells in a urine sample. Optionally the at least one biomarker is an Mcm protein, preferably Mcm5.

Kits

In an aspect of the invention there is provided a kit comprising a lysis buffer of the invention, a capture antibody and a detection antibody, wherein the capture antibody and the detection antibody bind to Mcm5. The kit can be used as part of an assay (for example an ELISA assay) to determine the concentration of Mcm5 in a sample. The lysis buffer can release Mcm5 from the cells in the sample. The capture antibody and detection antibody can be used to quantitate the concentration of Mcm5 in the sample.

Capture Antibody and Detection Antibody

A "capture antibody" is an antibody bound to the surface of a solid support for example an ELISA plate, also known as a mictrotitre plate. The "capture antibody" is able to bind to Mcm5 thus binding the Mcm5 to the solid support. In an embodiment a "capture antibody" is immobilised on an ELISA plate.

A "detection antibody" is an antibody which binds to a target such as Mcm5 and which can be used to detect the concentration of the target. For example, the antibody may be labelled either directly or indirectly by a detectable label. Alternatively the "detection antibody" may be labelled by contacting the detection antibody with a third antibody specific for the Fc region of the "detection antibody", in which case the third antibody should carry a label. Examples of suitable labels include enzymes (such as horse radish peroxidase, alkaline phosphatase, or glucose oxidase), radioactive isotypes (such as Europium$^{2+}$), DNA reporters, fluorogenic reporters, or electrochemiluminescent tags. In a preferred embodiment the "detection antibody" is labelled by conjugation to horse radish peroxidase.

Antibodies

The term "antibody" can refer to naturally occurring forms or recombinant antibodies such as single-chain antibodies, chimeric antibodies or humanised antibodies. The terms "antibody" and "antibodies" may also be considered to encompass fragments of antibodies that can bind to a target protein, such as an Mcm protein like Mcm5. Such fragments may include Fab'$_2$, F'(ab)$_2$, Fv, single chain antibodies or diabodies. In a preferred embodiment antibodies of the invention are naturally occurring, full length antibodies (rather than fragments). In a further preferred embodiment the antibodies are not humanised antibodies.

In general, antibodies are formed from two heavy chains and two lights chains. Each heavy chain is made up of heavy chain constant region (CH) and a heavy chain variable region (VH). Similarly each light chain is made up of light chain constant region (CL) and a light chain variable region (VL). The VH and VL regions comprise complementarity defining regions (CDRs). The CDRs are, primarily responsible for specific binding to the target protein.

Furthermore, an antibody of the invention will bind to an epitope (fragment) of Mcm5. Thus, the term "antibody which binds to Mcm5" refers to an antibody that binds to only a single epitope of Mcm5. Optionally an antibody that binds to Mcm5 is an antibody that "specifically binds" to Mcm5. The term "specifically binds" refer to antibody that binds to a target such as Mcm5 with a binding affinity that is at least 2-fold, 10-fold, 50-fold or 100-fold greater than its binding affinity for a non-target molecule.

A detection antibody may be conjugated to a label (for example Europium$^{2+}$ or Horseradish Peroxidase). The label may be directly attached or may be attached via a linker (such as Adipic Acid Dihyrazide or ADH).

The label may be attached by chemical conjugation. Methods of conjugating labels to antibodies are known in the art. For example, carbodiimide conjugated (Bauminger & Wilchek (1980) Methods Enzymol. 70, 151-159) may be used to conjugate labels to antibodies. Other methods for conjugating a label to an antibody can also be used. For example, sodium periodate oxidation followed by reductive alkylation or reduction amidation of appropriate reactants can be used, as can glutaraldehyde cross-linking. However, it is recognised that, regardless of which method of producing a conjugate of the invention is selected, a determination must be made that the conjugated antibody maintains its targeting ability and that the conjugated label maintains its function.

In a preferred embodiment the detection antibody is labelled by conjugation to Europium. This may be achieved using an EG&G Wallac DELFIA® Eu-labelling kit and following the manufacturer's protocol.

It is well within the ability of the person skilled in the art to develop an antibody that binds to Mcm5. This may be performed by immunising a mammal such as a mouse, rabbit or guinea pig, with Mcm5. It may be beneficial to include an adjuvant such as Freund's complete adjuvant. The spleen cells of the immunised mammal are removed and fused with myeloma cells to form hybridoma lines which are immortal given appropriate conditions and which secrete antibodies. The hybridomas are separated into single clones and the antibodies secreted by each clone are evaluated for their binding ability to Mcm5 protein.

Further Kit Components

In an embodiment the kit comprises a calibrator. The "calibrator" is a preparation of one or more known concentrations of Mcm5.

In an embodiment the kit comprises a substrate reagent. A substrate reagent can be used to detect the detection antibody. For example, where the "detection antibody" is conjugated to horse radish peroxidase the substrate reagent may comprise TMB (3,3',5,5'-tetramethylbenzidine), DAB (3,3'-diaminobenzidine) or ABTS (2,2'-azino-bis (3-ethylbenzothiazoline-6-sulphonic acid). In a preferred embodiment the substrate reagent comprises TMB. In a more preferred embodiment the substrate reagent is peroxide and TMB.

In an embodiment the kit further comprises a wash solution and/or a stop solution.

In an embodiment the kit is suitable for performing a sandwich ELISA.

Methods for Detecting the Presence of a Urological Cancer in a Subject

The present invention also provides methods for detecting the presence of urological cancer in a subject. Such methods are preferably in vitro methods. Such methods include a step of "performing an assay to determine the concentration" of at least one biomarker.

Performing an Assay to Determine the Concentration of a Biomarker (Such as an Mcm Protein)

In one embodiment of the invention the term "detecting the presence of a biomarker" can be considered to be substitutable with the term "performing an assay to determine the concentration" of a biomarker. In such embodiments, the presence of a biomarker can be considered to be detected, where its concentration is higher than a defined cutoff level.

Biological markers, or biomarkers, are molecules found in blood or other body fluids or tissues that help to indicate a biological state, process, event, condition or disease. It will be clear to those skilled in the art that biomarkers could consist of, but are not limited to DNA, RNA, chromosomal anomalies, proteins and their derivatives, or metabolites. In general terms, a biomarker may be regarded as a distinctive biological or biologically-derived indicator of a process, event or condition. In other words, a biomarker is indicative of a certain biological state, such as the presence of cancerous tissue. In some cases, different forms of biomarkers can be indicative of certain disease states. Alternatively merely the presence of elevated (or depressed) levels of the biomarker(s) of the present invention in body fluids such as blood and/or urine are indicative of urological cancer. In some embodiments biomarkers may be specific proteins or peptides whose occurrence, over-expression or under-expression in biological fluids such as urine (including urinary sediment), blood, saliva or semen may reflect the existence, progression, response to treatment or severity of urological cancer, such as prostate cancer.

Thus the term "biomarker" includes all biologically relevant forms of the protein or nucleic acid identified, including post-translationally modified polypeptides. For example, when the biomarker is a polypeptide the marker protein can be present in the sample in a glycosylated, phosphorylated, multimeric or precursor form.

There is no particular requirement that the concentration of, for example, the full length polypeptide (or nucleic acid) be scored. Indeed, it is possible that detection may take place by assaying particular fragments of a polypeptide of interest being present which are thus taken to indicate the presence of the overall biomarker polypeptide in the sample. This is especially true if the samples are analysed for example by mass spectrometry. Therefore the invention embraces the detection of fragments of the polypeptide (or nucleic acid) biomarkers. Moreover, the kits and peptides of the invention may comprise fragments of the polypeptides and need not comprise the full length sequences exemplified herein. Suitably the fragment is sufficiently long to enable its unique identification by immunological or mass spectrometry methods.

Thus for polypeptides a fragment is suitably at least 6 amino acids in length, suitably at least 7 amino acids in length, suitably at least 8 amino acids in length, suitably at least 9 amino acids in length, suitably at least 10 amino acids in length, suitably at least 15 amino acids, suitably at least 25 amino acids, suitably at least 50 amino acids, suitably at least 100 amino acids, or suitably the majority of the biomarker polypeptide of interest. Suitably a fragment comprises a small fragment of the biomarker polypeptide of interest, whilst being long enough to retain an identifiable amino acid sequence or mass.

The same considerations apply to nucleic acid nucleotide sequences. For nucleic acid sequences, a fragment is suitably at least 15 nucleotides in length, suitably at least 30 nucleotides in length, suitably at least 50 nucleotides in length, suitably at least 80 nucleotides in length, suitably at least 100 nucleotides in length, suitably at least 200 nucleotides in length, or suitably the majority of the sequence of interest.

Sequence Homology/Identity

Although sequence homology can also be considered in terms of functional similarity (i.e., amino acid residues having similar chemical properties/functions), in the context of the present document it is preferred to express homology in terms of sequence identity. Sequence comparisons can be conducted by eye or, more usually, with the aid of readily available sequence comparison programs. These publicly and commercially available computer programs can calculate percent homology (such as percent identity) between two or more sequences.

Percent identity may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues (for example less than 50 contiguous amino acids). For comparison over longer sequences, gap scoring is used to produce an optimal alignment to accurately reflect identity levels in related sequences having insertion(s) or deletion(s) relative to one another. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package, FASTA (Altschul et al., 1990, J. Mol. Biol. 215:403-410) and the GENE-WORKS suite of comparison tools.

In the context of the present document, a homologous amino acid sequence is taken to include an amino acid sequence which is at least 40, 50, 60, 70, 80 or 90% identical. Most suitably a polypeptide having at least 90% sequence identity to the biomarker of interest will be taken as indicative of the presence of that biomarker; more suitably a polypeptide which is 95% or more suitably 98% identical at the amino acid level will be taken to indicate presence of that biomarker. Suitably said comparison is made over at least the length of the polypeptide or fragment which is being assayed to determine the presence or absence of the biomarker of interest. Most suitably the comparison is made across the full length of the polypeptide of interest.

Specific biomarkers may be detected and/or quantified by interaction with a ligand or ligands, 1-D or 2-D gel-based analysis systems, liquid chromatography, combined liquid chromatography and any mass spectrometry techniques including MSMS, ICAT® or iTRAQ®, agglutination tests, thin-layer chromatography, NMR spectroscopy, sandwich immunoassays, enzyme linked immunosorbent assays (ELISAs), radioimmunoassays (RAI), enzyme immunoassays (EIA), lateral flow/immunochromatographic strip tests, Western Blotting, immunoprecipitation, particle-based immunoassays including using gold, silver, or latex particles and magnetic particles or Q-dots, or any other suitable technique known in the art.

The concentration of a biomarker such as Mcm5 may be detected and/or quantified by interaction with a ligand or ligands, 1-D or 2-D gel-based analysis systems, liquid chromatography, combined liquid chromatography and any mass spectrometry techniques including MSMS, ICAT® or iTRAQ®, agglutination tests, thin-layer chromatography, NMR spectroscopy, sandwich immunoassays, enzyme linked immunosorbent assays (ELISAs), radioimmunoassays (RAI), enzyme immunoassays (EIA), lateral flow/immunochromatographic strip tests, Western Blotting, immunoprecipitation, particle-based immunoassays including using gold, silver, or latex particles and magnetic particles or Q-dots, or any other suitable technique known in the art.

In certain aspects or embodiments of the invention the assay to determine the concentration of a biomarker is not an immunofluorometric assay. In such embodiments the assay is preferably an ELISA assay. In a further embodiment the ELISA assay is a sandwich ELISA assay. A sandwich ELISA assay comprises steps of capturing the biomarker to be assayed (such as an Mcm protein) using a "capture antibody" already bound to the plate, and detecting how much antigen has been captured using a "detection antibody". The detection antibody has been pre-conjugated to a label such as the enzyme HRP (Horse Radish Peroxidase). The ELISA plate with the labelled detection antibody is then washed to remove any excess unbound detection antibody. The washed plate is then exposed to an agent whose properties are changed by the label in a measurable manner. The concentration of the detection antibody may then be determined. For example if the detection antibody is conjugated to (labelled with) horseradish peroxidase, the ELISA plate may be exposed to TMB substrate. The concentration of the detection antibody, and therefore the concentration of Mcm5 in the original sample, may then be determined by quantitation of the colour change corresponding to the coversion of TMB into a coloured product.

The present invention comprises steps of performing an assay to determine the concentration of at least one biomarker in the urine sample. In a preferred embodiment the at least one biomarker comprises an Mcm protein, optionally Mcm5. In a further embodiment an abnormal value for the concentration of Mcm5 indicates an increased likelihood of a urological cancer in the subject.

Urological Cancers

The invention also provides methods for detecting a urological cancer. Such methods offer a significant advantage in that they will detect any tumours which are in intimate contact with the flow or urine in the urological system (i.e kidneys, ureters, bladder and urethra) of the patient being assayed.

Urological cancer includes all types of transitional cell carcinoma which might arise in the urological system. One example of transitional cell carcinoma is bladder cancer. However, transitional cells are present throughout the urological system including the lining of the renal pelvis, the ureters which conduct urine from the kidneys to the bladder and the urethra, as well as the wall of the bladder itself. Transitional cell carcinoma may arise in any of these locations.

It should be noted that there is a range of different sub-types of bladder cancer, i.e. there are types of bladder cancer other than transitional cell carcinoma, although this (transitional cell carcinoma) is the most common type of bladder cancer.

It is an advantage of the invention that other primary cancers such as penile cancer may also be detected, for example if they impinge on the urethral tract as it passes through the penis.

In addition, certain urological tumours may be detected even though they may not be in direct contact with the urine flow. One example is a prostate tumour which is not typically in contact with the urine flow, but from which cells exfoliate and exude into the urethra.

The invention also offers the advantage of being capable of detecting metastatic cancers, for example metastases of a different primary cancer which metastases have alighted in the urological system. In this embodiment, the invention is capable of detecting any cancer which either grew into the urological system (e.g., a colon cancer which may have invaded locally) or any cancer which has invaded through a metastasis (e.g., a remote primary cancer, which has given rise to one or more metastatic tumours within the urological system of the subject).

In one embodiment, the invention is advantageously applied to the detection of prostate cancer.

In one embodiment, the invention is advantageously applied to the detection of bladder cancer.

In one embodiment, the invention is applied to the detection of both prostate and bladder cancer.

Minichromosome Maintenance Proteins (Mcms)

Minichromosome maintenance (MCM) proteins have previously been used as diagnostic biomarkers for cervical cancer. Suitably a preferred biomarker according to the present invention is an Mcm protein. Most suitably the Mcm protein is Mcm5.

Elevated levels of a minichromosome maintenance complex (MCM) family protein such as the nuclear protein Mcm5 can be used to detect bladder cancer cells in urine sediments as well as prostate cancer. The assessment of Mcm5 is often carried out in a specialised laboratory with sophisticated instrumentation and highly skilled operatives (Stoeber et al. JNCI. 2002: 94: 1071-1079) and this style of analysis can be expensive or impractical to carry out in the pathology laboratory or point-of-care applications. However, it is an advantage that the inventors of the instant application have succeeded in developing a modified double-antibody sandwich ELISA format using a pair of specific monoclonal antibodies that is suited to the pathology laboratory and point-of-care applications to measure accurately Mcm5 levels in urinary sediments. However, this preferred type of assay does not confine the analysis of Mcm5 to this mode—according to the invention Mcm5 may be assayed according to any suitable method known in the art.

MCM proteins 2-7 comprise part of the pre-replication complexes which form on chromatin and which are essential prerequisites, or licensing factors, for subsequent DNA replication. The MCM protein complexes act as replicative helicases and thus are core components of the DNA replication machinery. MCMs are upregulated in the transition from the G0 to G1/S phase of the cell cycle and actively participate in cell cycle regulation. The MCM proteins form an annular structure around the chromatin.

The human Mcm5 gene maps to 22q13.1 and the mature Mcm5 protein consists of 734 amino acids (SEQ ID NO: 1; FIG. 1: UNIPROT P33992: HUMAN DNA replication licensing factor MCM5). The term "Mcm5" refers to a polypeptide of SEQ ID NO: 1, a polypeptide 85%, 90%, 95%, 98% or 100% identity to SEQ ID NO: 1.

The present invention usefully provides new assay methods for Mcm5 that are suited general clinical laboratory use and point-of-care applications.

Mcm5 is recorded as a concentration in urine. When the concentration exceeds a cut point there is an increased likelihood of urological cancer. The cut point can be set in a number of different ways. For example, it can be set at the mean of the values from healthy patients' urine plus a multiple of the standard deviation of values in the healthy population, usually a two or three times multiple. Alternatively the cut point may be set as the value generated by a known concentration of Mcm5-expressing dividing cells, exemplified by Stoeber et al (2002), who adopted as the cut point the number of counts in DELFIA generated from samples containing 1500 replicating cells per plate well.

Thus according to the present invention a presence of Mcm5 at greater than the mean plus two standard deviations of the concentration in healthy patients' urine, or the presence of Mcm5 at counts greater than the number of counts in DELFIA generated from samples containing 1500 replicating cells per plate well, indicates an increased likelihood of urological cancer.

In one embodiment an abnormal value for the presence of the Mcm protein indicates an increased likelihood of a urological cancer in a subject. In a further embodiment a method of the invention comprising a step of diagnosing a patient as having a urological cancer where the concentration of the Mcm protein determined by performing an assay is higher than the mean value from healthy patients plus a multiple of the standard deviation shown by the values derived from healthy subjects.

Antibodies

A number of anti-Mcm5 Antibodies suitable for use in the invention are available commercially. Examples are shown below:

| Name | Clone | Cat. No. | Supplier |
| --- | --- | --- | --- |
| CRCT5.1 | A2.7A3 | ab6154 | Abcam Ltd |
| MCM5 Antibody | 9H463 | MBS604829 | Mybiosource.com |
| anti-MCM5 | 2H8 | SAB1404056 | Sigma-Aldrich |
| Mcm5 monoclonal antibody | 3A7 | H00004174-M03A | Abnova Corp. |

Sample

Methods of the invention may comprise a step of "providing a sample from a subject". Preferably this step is non-invasive (not-surgical), for example collection of urine.

The sample may comprise any biological fluid such as blood, serum, saliva, semen, urine or urinary sediment, or an extract prepared from one of such fluids.

The sample is suitably urine.

Mcm5 is typically found in the nuclei of cells present in urine. Thus, suitably the sample comprises cells within the urine. More suitably, those cells may be concentrated by any known technique common in the art, such as filtration or more suitably centrifugal collection of the cells from urine. Enriching the cells from the urine may increase the signal, and may facilitate detection.

When testing for prostate cancer, most suitably the sample is first catch urine, such as may be obtained after massage of the prostate gland (when the subject is male).

Even more suitably, the sample may comprise the first few milliliters of first catch urine.

In other words, suitably the sample may comprise first pass urine, suitably first pass urine produced after massage of the prostate gland.

Even more suitably, the sample may comprise urinary sediment such as sedimented cells collected from urine (such as from total urine, or from first catch urine as explained above).

Assay Formats

In one aspect of the invention, an assay system is provided to determine the presence and/or concentration of biomarkers by detecting binding between biomarker and specific antibodies in a sandwich ELISA, or a two-site ELISA. Biomarkers may be determined separately (e.g. in physically separate assays, suitably carried out on fractions of the same sample). In this embodiment, in each assay the sample is contacted with a single ligand such as an antibody specific for the biomarker to be tested for. For example the sample may be added to different wells of a microtitre plate, wherein each well contains a different antibody.

Suitably the determination is carried out in an aqueous solution. The sample and/or the ligand (e.g. the antibody) may be present in solution. In some embodiments the antibody or sample may be immobilised on a solid support. Typically such a support may comprise the surface of the container in which the determination is being carried out, such as the surface of a well of a microtitre plate. In other embodiments the support may be a membrane (e.g. a nitrocellulose or nylon membrane) or a bead (e.g. latex or gold) or the surface of an array.

Determining whether the antibody binds (detects) a biomarker in the sample may be performed by any method known in the art for detecting binding between two moieties. The binding may be determined by measurement of a characteristic in either the antibody or biomarker (such as protein) that changes when binding occurs, such as a spectroscopic change.

In a preferred embodiment the determination is carried out using antibody as the ligand, which antibody is immobilised on a solid support. When the sample is contacted with the antibody, the biomarker molecules (such as protein molecules) in the sample bind to the antibody.

Optionally the surface of the solid support is then washed to remove any biomarker (such as protein) from the sample which is not bound to antibody. The presence of the biomarker bound to the solid support (through the binding with the antibody) can then be determined, indicating that the protein is bound to the antibody. This can be done for example by contacting the solid support (which may or may not have biomarker bound to it) with an agent that binds the protein specifically. This agent may be labelled, either directly or indirectly by a detectable label. Typically the agent is a second antibody, which is capable of binding the biomarker in a specific manner whilst the biomarker is bound to the first immobilised antibody. This second antibody can be labelled indirectly by contacting with a third antibody specific for the Fc region of the second antibody, wherein the third antibody carries a detectable label.

Another system which can be used to determine the binding between the biomarker protein and the antibody is a competitive binding system. One embodiment of such a system determines whether biomarker in the sample is able to inhibit the binding of the antibody to a reference compound which is capable of binding the antibody. If the biomarker protein in the sample is able to inhibit the binding between the antibody and reference compound then this indicates that such a sample contains the biomarker recognised by the antibody.

Reference Standard

The reference standard typically refers to a sample from a healthy individual i.e. one who has not suffered urological cancer.

The reference standard can be an actual sample analysed in parallel. Alternatively the reference standard can be one or more values previously derived from a comparative sample e.g. a sample from a healthy subject. In such embodiments a mere numeric comparison may be made by comparing the value determined for the sample from the subject to the numeric value of a previously analysed reference sample. The advantage of this is not having to duplicate the analysis by determining concentrations in individual reference samples in parallel each time a sample from a subject is analysed.

Suitably the reference standard is matched to the subject being analysed e.g. by gender e.g. by age e.g. by ethnic background or other such criteria which are well known in the art. The reference standard may be a number such as an absolute concentration determined by one or more previous studies.

Reference standards may suitably be matched to specific patient sub-groups e.g. elderly subjects, or those with a previous relevant history such as a predisposition to urological cancer.

Suitably the reference standard is matched to the sample type being analysed. For example the concentration of the biomarker polypeptide(s) being assayed may vary depending on the type or nature of the sample (e.g. conventional urine sample vs first catch sample after prostatic massage). It will be immediately apparent to the skilled worker that the concentration value(s) for the reference standard should be for the same or a comparable sample to that being tested in the method(s) of the invention. For example, if the sample being assayed is first catch urine then the reference standard value should be for first catch urine to ensure that it is capable of meaningful cross-comparison. In particular, extreme care must be taken if inferences are attempted by comparison between concentrations determined for a subject of interest and concentrations determined for reference standards where the nature of the sample is non-identical between the two. Suitably the sample type for the reference standard and the sample type for the subject of interest are the same.

It should be noted that for some embodiments of the invention, the protein concentrations determined may be compared to a previous sample from the same subject. This can be beneficial in monitoring the possibility of recurrence in a subject. This can be beneficial in monitoring the course and/or effectiveness of a treatment of a subject. In this embodiment the method may comprise further step(s) of comparing the value(s) determined for the sample of interest to one or more value(s) determined for the same biomarker(s) from different samples such as samples taken at different time points for the same subject. By making such a comparison, information can be gathered about whether a particular marker is increasing or decreasing in a particular subject. This information may be useful in diagnosing or predicting changes over time, or changes inhibited or stimulated by a particular treatment or therapy regime, or any other variable of interest.

In this way, the invention can be used to determine whether, for example after treatment of the patient with a drug or candidate drug, or by tumour resection, the disease has progressed or not, or that the rate of disease progression has been modified. The result can inform the pathway of further treatment.

Ligands/Antibodies

The preferred modes of determining the presence and/or concentration of the biomarkers that are discussed herein make use of suitable antigen binding molecules or ligands that bind specifically to the selected biomarkers. Suitably the ligand may be an antibody, or an antibody derivative such as an scFv, or Fab.

Method for Preparing Cells from a Urine Sample

The invention provides a method for preparing cells from a urine sample.

In an embodiment, urine from a urine sample is passed through a filter for capturing cells, such that cells in the urine sample are captured in the filter. The volume of urine passed through the filter is preferably between 1 ml and 100 ml, more preferably between 30 ml and 70 ml, and even more preferably about 50 ml.

A lysis buffer (optionally a lysis buffer of the invention) is then passed through the filter, such that cells are exposed to the lysis buffer. The lysis buffer may be capable of releasing at least one biomarker from cells. The lysis buffer is passed at least once through the filter to expose the cells to the lysis buffer such that at least one biomarker is released from the cells. In other embodiments, it may be necessary to pass the lysis buffer through the filter a plurality of times, e.g. at least twice, at least three times or at least four times. This helps to fully saturate the filter with the lysis buffer, so that the at least one biomarker is more effectively released from the captured cells. In the case where the lysis buffer is passed a plurality of times through the filter, the lysis buffer is preferably alternately passed through the filter upstream and downstream (i.e. in opposite directions) to help with fully saturating the filter with lysis buffer. The volume of lysis buffer (i.e. the volume of lysis buffer flowing through the filter in one pass) is preferably between 250 µl and 1000 µl, more preferably between 300 µl and 500 µl, and even more preferably about 500 µl.

After exposing the captured cells to the lysis buffer, the filter is then incubated for a period of time such that the lysis buffer releases at least one biomarker from the cells resulting in a lysis buffer comprising the at least one biomarker released from the cells (lysate). The incubation time of the filter is preferably between 5 minutes and 1 hour, more preferably between 20 minutes and 30 minutes, and even more preferably about 10 minutes. Suitably "incubating the filter" comprises maintaining the lysis buffer in contact with the filter for a period of time. Suitably a filter is incubated at a fairly constant temperature (varying by less than 5° C. during the incubation period). Optionally the temperature in between 15° C. and 30° C., preferably around room temperature. Optionally, after the filter has been incubated, lysis buffer is passed through the filter again at least once.

Apparatus for Preparing Cells from a Urine Sample

The present invention also provides an apparatus for preparing cells from a urine sample. In the description of the apparatus below, the terms "upstream" and "downstream" are defined relative to the direction of flow of urine through the apparatus, i.e. flow from the inlet to the outlet is flow in a downstream direction. Components of the apparatus described as being in "fluid communication" with each other means that a fluid is able to flow between these components although it may not be able to flow any further (e.g. in the case of a closed valve). Such components could be connected via means known in the art, e.g. a tube or a pipe. Each component of the apparatus may be removably connected to other components. Some or all of the components of the apparatus may be integrally formed.

Figure 18:
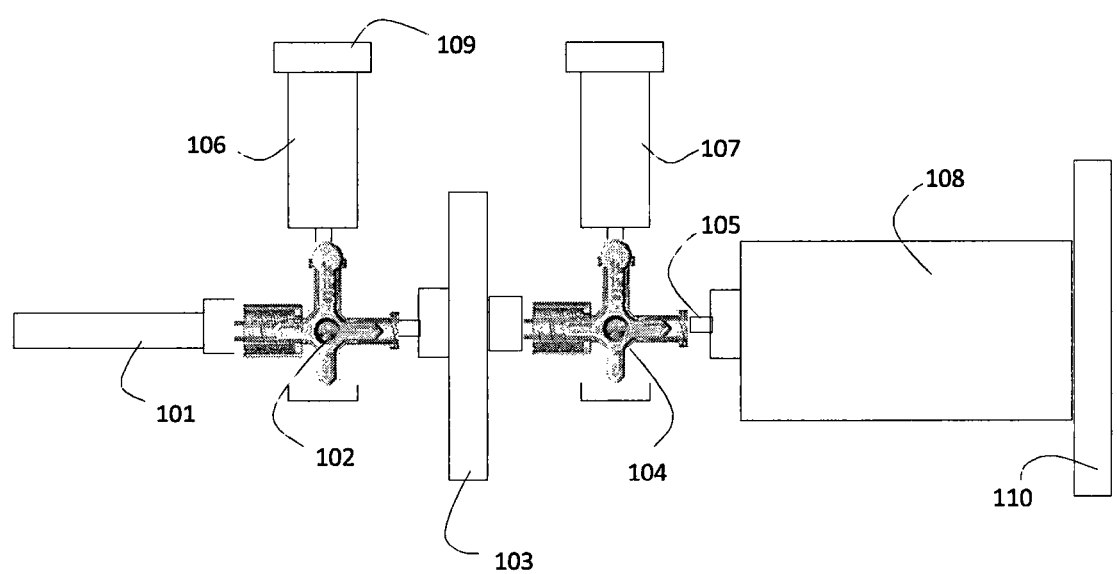
FIG. 18 depicts an apparatus for preparing cells from a urine sample.

FIG. 18 shows an embodiment of the apparatus 100. The apparatus 100 comprises an inlet 101 through which urine from a urine sample is able to pass into the apparatus (from the left, as depicted) when in use. The inlet 101 optionally comprises a one-way valve (not shown) to prevent fluid from passing back out of the apparatus (i.e. upstream of the inlet). A first valve 102 is arranged downstream of the inlet 101 and is in fluid communication with the inlet 101. The first valve 102 is not limited to a particular valve type, as long as it can be configured to open or block fluid communication between different parts of the apparatus as required. Such configurations will be explained in further detail below. The first valve 102 is optionally a luer valve. The first valve 102 is optionally a 3-way or 4-way valve.

A filter 103 is arranged downstream of the first valve 102 and is in fluid communication with the first valve 102. The filter 103 is suitable for capturing cells from urine as urine flows through the filter. The filter 103 preferably prevents spherical particles having a diameter greater than 15 µm, 10 µm or 5 µm from passing through, while allowing smaller particles to pass through. For non-spherical particles, the filter 103 preferably prevents equivalent spherical particles having a diameter greater than 15 µm, 10 µm or 5 µm from passing through, the equivalent spherical particles having the same volume as the non-spherical particles. The diameter $d_v$ of such an equivalent spherical particle is given by the equation $$d_v = 2\sqrt[3]{\frac{3V}{4\pi}},$$

where V is the volume of the non-spherical particle. The filter 103 optionally has a pore structure with a pore size (pore diameter) of about 15 µm, about 10 µm or about 5 µm. The filter 103 preferably has a pore structure with a pore size (pore diameter) between 1 and 6 µm, more preferably between 4 and 6 µm, and even more preferably about 5 µm. However, the type of filter is not limited, as long as it is suitable for capturing cells from urine as urine flows through the filter. The filter 103 could optionally have a mesh structure rather than a pore structure, for example.

A second valve 104 is arranged downstream of the filter 103 and is in fluid communication with the filter 103. The second valve 104 is not limited to a particular valve type, as long as it can be configured to open or block fluid communication between different parts of the apparatus as required. Such configurations will be explained in further detail below. The second valve 104 is optionally a luer valve. The second valve 104 is optionally a 3-way or 4-way valve.

An outlet 105 through which urine able to the flow out while the apparatus is in use is arranged downstream of the second valve 104 and is in fluid communication with the second valve 104. The outlet 105 optionally comprises a valve (not shown) to block fluid from passing out through the outlet 105 when required.

A first buffer reservoir 106 for holding a lysis buffer is provided. The first buffer reservoir 106 is in fluid communication with the first valve 102. The first buffer reservoir 106 is preferably sized to hold at least 500 µl of lysis buffer, more preferably at least 1 ml of lysis buffer, and even more preferably at least 5 ml of lysis buffer. The first buffer reservoir 106 is optionally sized to hold a maximum of 50 ml lysis buffer, more preferably a maximum of 25 ml lysis buffer, and even more preferably a maximum of 10 ml lysis buffer. The first buffer reservoir 106 is optionally a syringe but any container suitable for holding a lysis buffer could be used.

A second buffer reservoir 107 for holding a lysis buffer is also provided. The second buffer reservoir 107 is in fluid communication with the second valve 104. The second buffer reservoir 107 is preferably sized to hold at least 500 µl of lysis buffer, more preferably at least 1 ml of lysis buffer, and even more preferably at least 5 ml of lysis buffer. The second buffer reservoir 107 is optionally sized to hold a maximum of 50 ml lysis buffer, more preferably a maximum of 25 ml lysis buffer, and even more preferably a maximum of 10 ml lysis buffer. The second buffer reservoir 107 is optionally a syringe but any container suitable for holding a lysis buffer could be used.

Configurations of the first and second valves 102, 104 will now be described.

In a first configuration of the first and second valves 102, 104, fluid communication between the first buffer reservoir 106 and the filter 103 is blocked, fluid communication between the second buffer reservoir 107 and the filter 103 is blocked, and fluid communication between the inlet 101, filter 103 and outlet 105 is open. In this first configuration, urine is able to flow from the inlet 101 to the outlet 105 via the filter 103 while the apparatus is in use. In the first configuration, preferably, urine is not able to flow from the inlet 101 or the outlet 105 to the first and/or second buffer reservoirs 106, 107. In the first configuration, preferably, lysis buffer is not able to flow from the first buffer reservoir 106 to the inlet 101 or to the outlet 105. In the first configuration, preferably, lysis buffer is not able to flow from the second buffer reservoir 107 to the inlet 101 or to the outlet 105.

In a second configuration of the first and second valves 102, 104, fluid communication between the first buffer reservoir 106 and the filter 103 is open, fluid communication between the second buffer reservoir 107 and the filter 103 is open and flow through the inlet 101 and out the outlet 105 is blocked. In this second configuration, lysis buffer is able to flow between the first buffer reservoir 106 and the second buffer reservoir 107 via the filter 103 while the apparatus is in use. In the second configuration, preferably, lysis buffer is not able to flow from the first buffer reservoir 106 to the inlet 101 or to the outlet 105. In the second configuration, preferably, lysis buffer is not able to flow from the second buffer reservoir 107 to the outlet 105 or to the inlet 101. In the second configuration, preferably, urine is not able to flow between the inlet 101 and the outlet 105.

In the second configuration, a closed system is preferably formed between the first buffer reservoir 106, the filter 103 and the second buffer reservoir 107. Thus, when a volume of lysis buffer flows out of the first buffer reservoir 106, an equal volume of lysis buffer preferably flows into the second buffer reservoir 107 and vice versa. Thus, at a given point in time when the apparatus is in use, lysis buffer is provided in one or both of the first and second buffer reservoirs 106, 107. In other words, at a given point in time when the apparatus is in use, (i) lysis buffer is present in the first buffer reservoir 106 but not in the second buffer reservoir 107; (ii) lysis buffer is present in the second buffer reservoir 107 but not in the first buffer reservoir 106; or (iii) lysis buffer is present in both the first and second buffer reservoirs 106, 107.

The apparatus 100 optionally comprises a urine reservoir 108 for holding urine. The urine reservoir 108 is arranged downstream of the outlet 105 and is in fluid communication with the outlet 105. The urine reservoir 108 is preferably sized to hold at least 10 ml urine, more preferably at least 25 ml urine, and even more preferably at least 50 ml urine. The urine reservoir 108 is optionally sized to hold a maximum of 1000 ml urine, more preferably a maximum of 500 ml urine, and even more preferably a maximum of 250 ml urine. In the first configuration of the first and second valves 102, 104, urine is able to flow from the inlet 101 through to the urine reservoir 108 via the filter 103 and outlet 105. The urine reservoir 108 is thus configured to hold urine that has been filtered through the filter 103 while the apparatus is in use. The outlet 105 may be reversibly blocked using a valve or sealing means (not shown) to prevent urine from flowing from the urine reservoir 108 back through the outlet 105 (i.e. in an upstream direction). The urine reservoir may be removably connected to the outlet 105.

The apparatus 100 optionally comprises means 110 for providing a flow of urine. Such means can be, for example, a pump or part of a syringe. When using a syringe, the syringe can provide both the urine reservoir 108 and the means 110 for providing a flow of urine. In that case, a flow of urine can be provided by drawing the syringe of the urine reservoir 108, causing urine to flow from the inlet 101 into the urine reservoir 108. In another embodiment, a flow of urine may be provided by "pushing" a urine sample through the apparatus from the inlet 101, using a syringe in fluid communication with the inlet 101, for example.

The apparatus 100 optionally comprises means 109 for providing a flow of lysis buffer. Such means can be, for example, a pump or part of a syringe. When using a syringe, the syringe can provide both the first buffer reservoir and means 109 for providing a flow of lysis buffer. Similarly, if second buffer reservoir 107 is part of a syringe, the second buffer reservoir can act as means 109 for providing a flow of lysis buffer. If both the first and second buffer reservoir 106, 107 are provided by syringes, then both can act as means 109 for providing a flow of lysis buffer.

The invention also provides a device for analysing a urine sample from a subject. The device comprises the above-described apparatus 100 and an assay device capable of determining the concentration of at least one biomarker in the urine sample. The assay device preferably comprises a first antibody that is immobilised and a second detection antibody. The device is preferably arranged such that the lysate may flow past the immobilised antibody (e.g. by lateral flow) and the biomarker may bind the immobilised antibody. The amount of bound biomarker may be detected using the detection antibody. The assay device may be provided as a separate component, unconnected to the apparatus 100, or may be integral or connectable to the apparatus 100 so as to be in fluid communication with the apparatus 100. The assay device is preferably configured to receive lysate from the apparatus 100. In the case that the assay device is in fluid communication with the apparatus 100, the first and second valves may be configured in a third configuration, such that lysate is able to flow from either the first buffer reservoir 106 or the second buffer reservoir 107 to the assay device.

For example, in one embodiment, the first valve 102 is configured to allow flow from the first buffer reservoir 106 to the assay device. In this case, preferably, fluid communication between the first buffer reservoir 106 and the second buffer reservoir 107 is blocked. In another embodiment, the second valve 104 is configured to allow flow from the second buffer reservoir 107 to the assay device. In this case, preferably, fluid communication between the first buffer reservoir 106 and the second buffer reservoir 107 is blocked.

The first valve 102 is an example of a first valve arrangement and the second valve 104 is an example of a second valve arrangement that enable the path of fluids through the apparatus to be controlled according to the above described first and second (and optionally third) configurations. However, the first valve arrangement is not limited to one valve. The first valve arrangement may comprise a plurality of valves. For example, in the case that the first valve arrangement comprises two valves, one valve could be arranged to open and block fluid communication between the inlet 101 and the filter 103, and the other valve could be arranged to open and block fluid communication between the first buffer reservoir 106 and the filter 103. Similarly, the second valve arrangement is not limited to one valve. The second valve arrangement may comprise a plurality of valves. For example, in the case that the second valve arrangement comprises two valves, one valve could be arranged to open and block fluid communication between the filter 103 and the outlet 105, and the other valve could be arranged to open and block fluid communication between the second buffer reservoir 107 and the filter 103.

Method of Using the Apparatus

The invention also provides a method of using the apparatus 100. As before, the terms "upstream" and "downstream" are defined relative to the direction of flow of urine through the apparatus, i.e. flow from the inlet to the outlet is flow in a downstream direction.

Urine from a urine sample is flowed through the inlet 101 to the outlet 105 via the filter 103, with the first valve arrangement (e.g. the first valve 102) and second valve arrangement (e.g. the second valve 104) configured in the first configuration. This causes cells in the urine to be captured in the filter 103, while filtered urine passes out the outlet 105 and optionally into the urine reservoir 108. The flow of urine is optionally provided by means 110 for providing a flow of urine.

An inert gas (e.g. air) is then preferably flowed through the inlet 101 to the outlet 105 to remove any residual volume of urine in the apparatus. This can be achieved using the means 108 for providing a flow of urine, for example, by flowing an inert gas from the inlet to the outlet. Alternatively, a separate means for providing a flow of inert gas may be provided.

The outlet 105 is then preferably blocked or sealed to prevent urine from passing back through the outlet in an upstream direction.

The first and second valves 102, 104 are then configured into the second configuration, thereby forming a closed system between the first buffer reservoir 106, the filter 103 (containing the cells) and the second buffer reservoir 107. Lysis buffer contained in the first buffer reservoir 106 is then passed to the second buffer reservoir 107 via the filter 103 or vice versa. The lysis buffer is passed at least once through the filter 103 to expose the cells to the lysis buffer such that at least one biomarker is released from the cells. In other embodiments, it may be necessary to pass the lysis buffer through the filter 103 a plurality of times, e.g. at least twice, at least three times or at least four times. This helps to fully saturate the filter with the lysis buffer, so that the at least one biomarker is more effectively released from the captured cells. In the case where the lysis buffer is passed a plurality of times through the filter, the lysis buffer is preferably alternately passed through the filter upstream and downstream (i.e. in opposite directions) to help with fully saturating the filter with lysis buffer.

The filter 103 is then incubated for a period of time such that the lysis buffer causes at least one biomarker to be released from the cells. The incubation is preferably carried out for a period of time between 10 seconds and 5 hours, more preferably between 30 seconds and 1 hour, and even more preferably about 10 minutes. Suitably "incubating the filter" comprises maintaining the lysis buffer in contact with the filter for a period of time. Suitably a filter is incubated at a fairly constant temperature (varying by less than 5° C.). Optionally the temperature in between 15° C. and 30° C., preferably around room temperature. The lysis buffer containing the at least one biomarker released from the cells (the lysate) is then optionally passed back into one of the first and second buffer reservoirs 106, 107.

In the case of the device for analysing a urine sample from a subject comprising the apparatus 100 and the assay device, the lysis buffer containing the at least one biomarker can then be passed to the assay device. In the case that the assay device is in fluid communication with the apparatus 100, this can be achieved by configuring the first and second valves 102, 104 into the third configuration and then passing the lysate containing the at least one biomarker into the assay device. In the case that the assay device is not in fluid communication with the apparatus 100, the lysate can be externally passed from the apparatus 100 to the assay device.

The invention is now described by way of examples, which are intended to be illustrative rather than restrictive in nature.

EXAMPLES

All chemicals were purchased from Sigma-Aldrich unless otherwise noted.

Example 1

Materials

Single voided urine specimens were obtained from patients attending a haematuria clinic at Heatherwood Hospital (Heatherwood and Wexham Park Hospitals NHS Foundation Trust), having obtained ethical approval from the Local Research Ethics Committee. Urinalysis using Multistix 10 SG dipsticks (Siemens) was carried out on fresh samples and the remainder of the urine was dispensed into 1 ml or 15 ml Falcon tubes which were placed in dry ice for transport to the laboratory.

Mcm5

Figure 3:
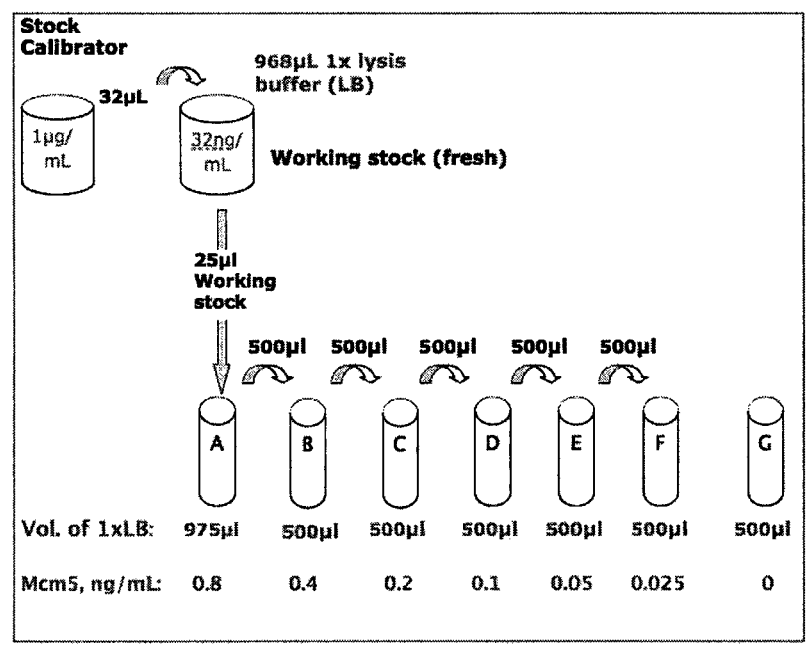
FIG. 3 shows a diagram describing how to dilute the stock calibration solution.

An embodiment of the invention is a simple ELISA test for Mcm5, which usefully replaces the specialized and complex Mcm5 DELFIA® test (see Stoeber et al 2002 (Journal of the National Cancer Institute, 94, 1071-1079; 2002), thus the test could be carried out in a typical clinical chemistry laboratory. The test is a direct double-monoclonal antibody sandwich enzyme-linked immunoassay. Both antibodies have high affinity and specificity for the antigen Mcm5. Any Mcm5 in the sample under test is captured by a specific monoclonal antibody bound to the surface of the microtitre plate well. Detector antibody is then added, which binds to a different site on the antigen and which is linked to the enzyme horseradish peroxidase (HRP). The presence and amount of HRP retained in plate wells is assessed by measuring the intensity of colour that develops after the addition of tetramethylbenzidine (TMB), which is a chromogenic substrate of HRP. Optical density is proportional to the concentration of Mcm5 in the sample within defined limits. By testing a range of concentrations of Mcm5, a dose-response curve can be generated from which the antigen concentration of an unknown can be ascertained (see FIGS. 2 and 3).

Two monoclonal antibodies (mAbs) are used in the assay, 12A7 and 4B4. The antibodies were obtained from Cancer Research Technology Ltd (CRT) under a non-exclusive licensing agreement with the applicant. For ELISA tests, mAb 12A7 was used for plate coating, and mAb 4B4 for detection.

Specimen collection and preparation: The test can be performed on human urine. Samples should be collected in, for example, 150 mL plastic bottles with a screw cap, which should be clean but not necessarily sterile. The collection bottle should not contain any preservative and ideally should be of a volume of greater than 100 mL. Samples may be stored for up to 4 hours at 2-8° C. prior to use. To prepare urine specimens for assay 30 mL of the sample is transferred to a 50 mL plastic centrifuge tube with screw cap After centrifugation for 5 min at 1,500 g the supernatant is carefully decanted and treated as waste according to local H&S guidelines. The tubes are placed inverted on absorbent paper and excess liquid is allowed to drain. 250 μl Lysis/sample buffer is added to the pellet; the pellet is resuspended using an adjustable pipette with disposable tip.

Reagents: Test components are described herewith in the form of a kit (see Table 1). Each kit contains sufficient materials for a single 96-well microplate, or 80 determinations in duplicate wells if the whole plate is used at one time.

TABLE 1

| MCM5 kit contents | Quantity |
| --- | --- |
| Anti-MCM5 antibody coated microplate comprising twelve 8-well strips coated with mouse monoclonal anti-MCM5 antibody and a stabiliser packed in a sealed foil pouch with desiccant. | 1 microtitre plate, 96 wells |
| Wash solution, 20x concentrate. PBS buffer containing TWEEN ® 20 at 0.05% after dilution to 1 litre in deionized water. | 1 × 50 mL |
| Anti-MCM5 antibody-HRP conjugate. Mouse anti-MCM5 monoclonal antibody conjugated to horseradish peroxidase (HRP) at working concentration in a buffered solution containing protein and an anti-microbial agent. | 1 × 11 mL |
| TMB substrate reagent. A colourless solution that develops a blue colour in the presence of HRP. | 1 × 11 mL |
| Stop solution. Aqueous 1M hydrochloric acid. Personal protective equipment is recommended to avoid direct exposure. | 1 × 11 mL |
| Lysis/running buffer. An aqueous solution containing a buffering agent and a mild detergent. | 1 × 15 mL |
| Calibrator set. Vials containing lyophilised purified MCM5 protein at concentrations of 900, 300, 100 and 33 pg/mL, to be reconstituted in 1 mL lysis/running buffer. | 4 vials |
| Controls set. Vials containing lyophilised protein/cells. | 2 vials |
| Adhesive material. For sealing the plate wells during incubations. | 1 sheet |
| Instructions for Use. Also available at urosens.com | 1 copy |

In addition to the constituents listed in Table 1, the following additional materials are helpful and may optionally be provided in a kit of the invention. These materials are to be regarded as separately disclosed and may therefore be individually added to the kit of the invention. Pipette(s) capable of delivering 50 μl and 100 μl volumes with a precision of better than 1.5%; dispenser(s) for repetitive deliveries of 100 μl and 300 μl volumes with a precision of better than 1.5%; microplate washer or a squeeze bottle (optional); a microplate reader with 450 nm and 620 nm wavelength absorbance capabilities, absorbent paper for blotting the microplate wells and plastic wrap or microplate covers for incubation steps plus a timer.

Test Procedure: Before proceeding with the assay, all reagents should be brought to room temperature (20-27° C.) for 30 minutes. Unused reagents are stored at 2-8° C. after use. Sufficient microplate well strips are removed for each sample to be tested, including a dilution series of calibrators and quality control samples, to be assayed in duplicate. 100 μL of the appropriate calibrator—or specimen is pipetted into the assigned well which is incubated at room temperature (20-27° C.) for thirty (30) minutes on a rotary microtitre plate shaker at 700 rpm. The contents are discarded and the wells washed by six changes of 300 μl of wash buffer. 100 μl of the Anti Mcm5 HRP Antibody reagent/conjugate is then added to each well. After mixing, the wells are incubated stationary for 30 minutes at room temperature (20-27° C.). The contents of the microplate are then discarded by decantation or aspiration. If decanting, tap and blot the plate dry with absorbent paper and then wash the wells as described above. 100 ul of Substrate Reagent is then added to all wells and incubated at room temperature (20-27° C.) for thirty 30 minutes. The reaction is stopped by addition of 100 uL of stop solution to each well. The absorbance in each well is read at 450 nm (using a reference wavelength of 620-630 nm to minimize well imperfections) in a microplate reader. The results should be read within 30 minutes of adding the stop solution.

Calibrator samples are provided. These are prepared using a serial dilution at the time of the assay and discarded after use (see FIG. 3).

To interpret the results a dose-response curve is used to ascertain the concentration of Mcm5 in unknown specimens. This can be constructed manually or automatically using a computer programme. For manual calculation, record the absorbance obtained from the printout of the microplate reader. Plot the absorbance for each duplicate dilution versus the corresponding Mcm5 concentration in ng/mL on linear graph paper then draw the best-fit curve through the plotted points. To determine the concentration of Mcm5 for an unknown, locate the average absorbance of the duplicates for each unknown on the vertical axis of the graph, find the intersecting point on the curve, and read the concentration (in ng/ml) from the horizontal axis of the graph.

Table 2 illustrates the results from a typical experiment.

TABLE 2

| Sample ID | Value (pg/ml) | Well number | Abs (A) | Mean Abs (B) |
| --- | --- | --- | --- | --- |
| CAL G (blank) | 0 | A1 | 0.082 | 0.083 |
|  |  | B1 | 0.084 |  |
| CAL F | 25 | C1 | 0.164 | 0.163 |
|  |  | D1 | 0.162 |  |
| CAL E | 50 | E1 | 0.245 | 0.242 |
|  |  | F1 | 0.239 |  |
| CAL D | 100 | G1 | 0.395 | 0.393 |
|  |  | H1 | 0.390 |  |
| CAL C | 200 | A2 | 0.693 | 0.681 |
|  |  | B2 | 0.669 |  |
| CAL B | 400 | C2 | 1.281 | 1.252 |
|  |  | D2 | 1.222 |  |
| CAL A | 800 | E2 | 2.458 | 2.342 |
|  |  | F2 | 2.226 |  |

The Mcm5 procedure has an analytical detection limit of <7 pg/ml.

Example 2—Clinical Study of Mcm5 in 116 Subjects being Investigated for Bladder Cancer Urine specimens were obtained from 116 patients the majority of whom were subsequently examined by flexible cystoscopy and scanning by CT or ultrasound. If abnormal results were obtained the patients were referred for biopsy. Where available the results of these investigations were collected and added to the data set. The levels of Mcm5 were measured in each subject using the ELISA technique described above (Example 1). Eight cases of bladder cancer were clinically confirmed of which five were scored as positive in the Mcm5 assay.

TABLE

In the table "+" indicates that the Mcm5 assay result exceeded the mean of the known negatives + 3 SDs (negative mean OD 0.05, SD 0.0593). Therefore the cut point was arbitrarily set at OD 0.23.

| Patient ID Number | Grade/Stage Location | ELISA result |
| --- | --- | --- |
| 6 | G2 pTa, papillary tumour, bladder | + |
| 25 | pTa, ureter | − |
| 27 | G2 pTa, papillary tumour, bladder | − |

TABLE-continued

In the table "+" indicates that the Mcm5 assay result exceeded the mean of the known negatives + 3 SDs (negative mean OD 0.05, SD 0.0593). Therefore the cut point was arbitrarily set at OD 0.23.

| Patient ID Number | Grade/Stage Location | ELISA result |
| --- | --- | --- |
| 57 | G1 pTa, 5 mm tumour, bladder | − |
| 86 | Squamous cell carcinoma, bladder | + |
| 92 | Squamous cell carcinoma, bladder | + |
| 96 | G3 pT2, bladder (gross haematuria) | + |
| 115 | G3 pT2, bladder | + |

There were also four cases in which a positive ELISA result occurred in the absence of a confirmed diagnosis of malignancy: Patient 13 (Papillary lesions were observed in the bladder; biopsy result was not recorded. Prostate occlusive); Patient 30 (No other pathology recorded); Patient 65 (Nephrectomy recorded); Patient 101 (enlarged prostate with calcification). It is known that the presence of calculi can cause false positive results due to the abrasive effect of the material on the basal layer of the epidermis leading to release of MCM+ cells, but rate of such cases is too small to impact on the present assay.

Assay Statistics

Standard assay statistics were calculated for the Mcm5 assay data. Although the true clinical end-point was not available for all patients in the study, the skilled person will appreciate that this modest panel has yielded convincing results. In particular the study has provided a realistic estimate of specificity of 96% (104/108).

Example 3—Comparison of Various Buffers

Figure 4:
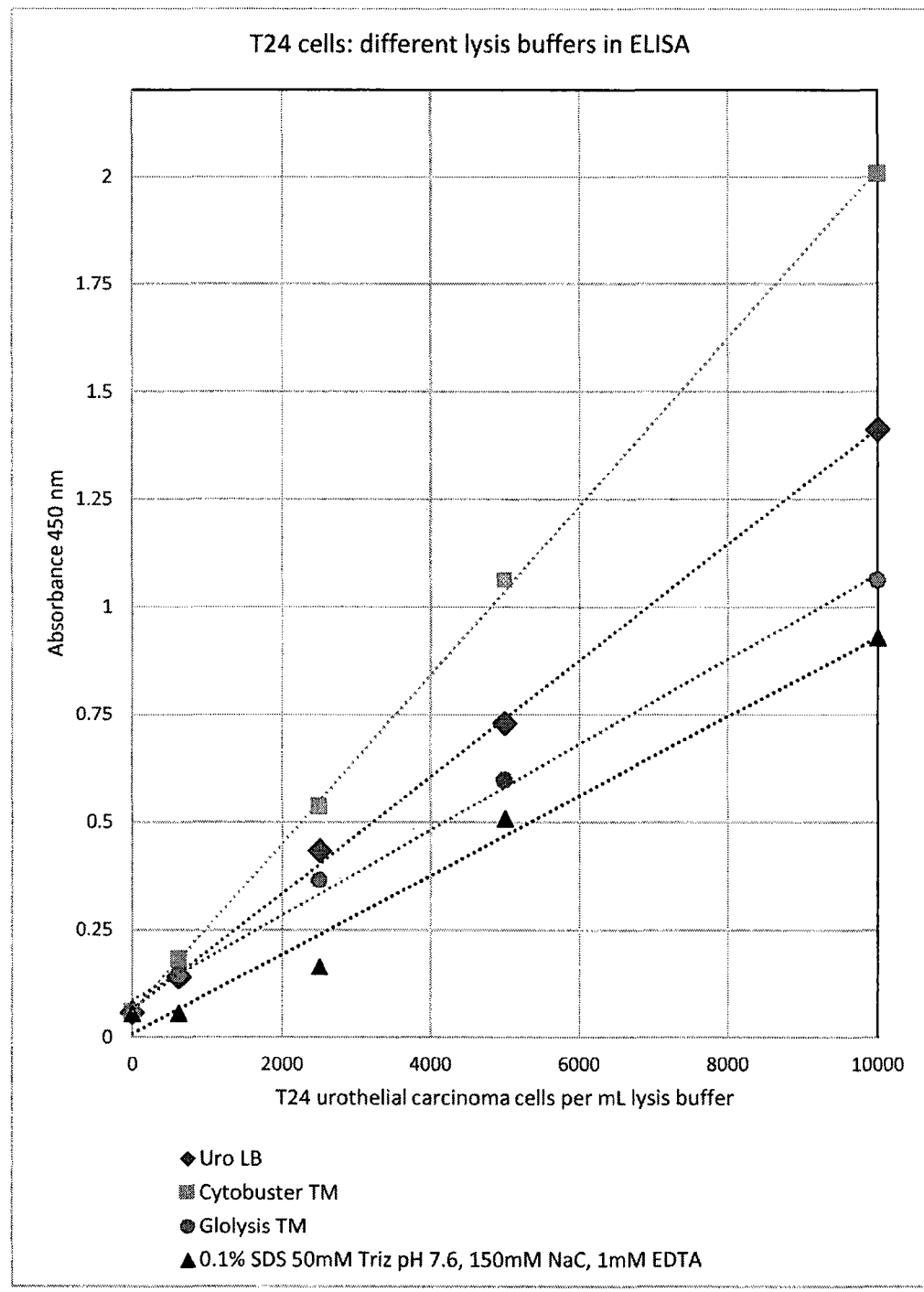
FIG. 4 shows a graph comparing the amount of Mcm5 released from urothelial carcinoma cells after exposure to 4 different lysis buffers (Uro LB "0.08% sodium deoxycholate, 0.08% CHAPS, 2 mM EDTA, 150 mM TRIZMA® (tris(hydroxymethyl)methylamine (Tris) hydrochloride) pH 7.6", CYTOBUSTER™ Protein Extraction Reagent, Glo Lysis Buffer, and 0.1% SDS, 50 mM TRIZMA® pH 7.6, 150 mM NaCl, 1 mM EDTA).

Known numbers of T24 urothelial carcinoma cells were lysed in each buffer and the lysates tested in ELISA for Mcm5. The results demonstrate a marked difference in lysis efficiency in this assay. The buffer containing SDS is typical of those described in the literature but is significantly less efficient than CYTOBUSTER™ Protein Extraction Reagent or 'Urosens LB' (0.08% sodium deoxycholate, 0.08% CHAPS, 2 mM EDTA, 150 mM TRIZMA® pH 7.6). The results are presented in FIG. 4.

Example 4

Figure 5:
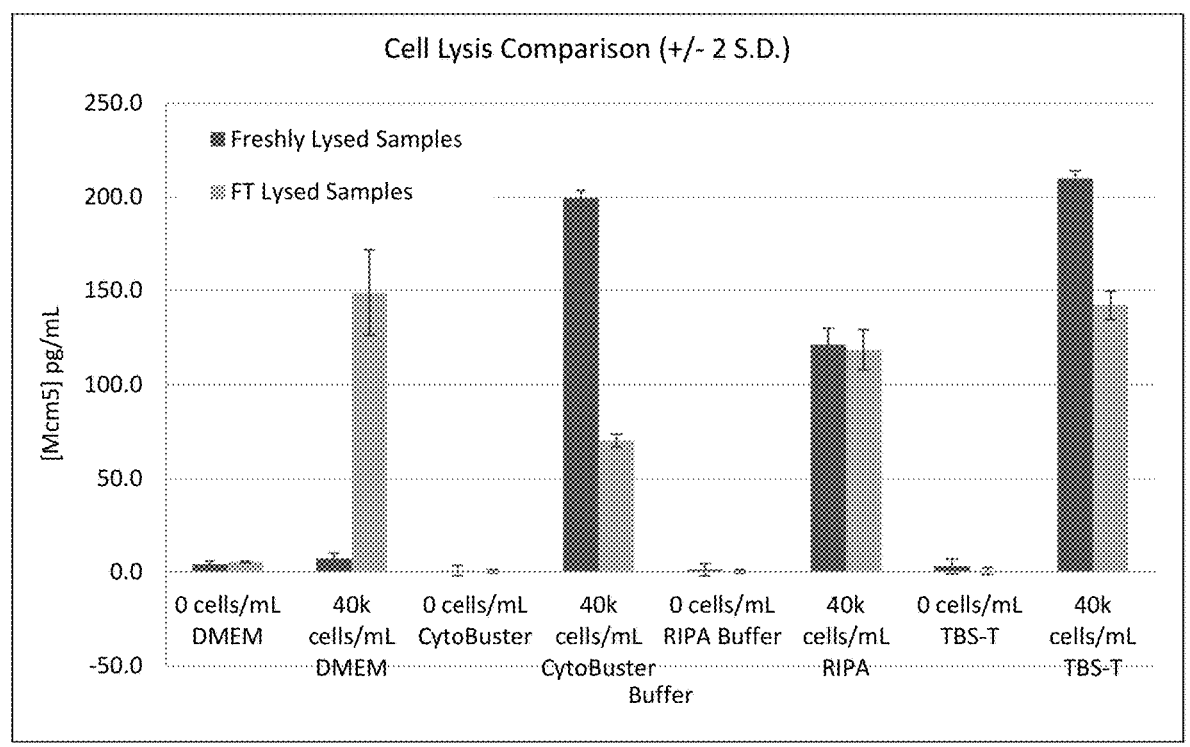
FIG. 5 shows a graph comparing CYTOBUSTER™ Protein Extraction Reagent, radioimmunoprecipitation assay (RIPA) buffer and Tris buffered saline with TRITON™ X-100 (TBS-T Buffer) prior to modification.

The lysis of cells in CYTOBUSTER™ Protein Extraction Reagent was compared to cells in TBS TRITON™ buffer (TBST) and RIPA buffer with a control of cell pellets reconstituted in DMEM (cell culture medium). The results are described in FIG. 5.

The potency of Mcm5 in the lysed samples was tested after application of buffer to cells. Some samples were frozen after exposure to buffer and before testing. Ideally, a universal buffer that would be used in both scenarios would be useful.

The control results proved that when fresh samples were tested, the cells remain intact when no lysing agent is added, but post-freeze-thaw (FT), the cells burst by mechanical breakdown of the cell membrane, thereby releasing Mcm5. This experiment showed that when fresh lysates are used, the TBST buffer is roughly equivalent to the CYTOBUSTER™ Protein Extraction Reagent. However, after samples have been frozen, the CYTOBUSTER™ Protein Extraction Reagent lysates undergo a drastic loss of potency, whereas the TBST is not as strongly affected. The RIPA lysates buffer, although lower when derived from fresh sample retains all of the potency post-FT.

Example 5

Figure 6:
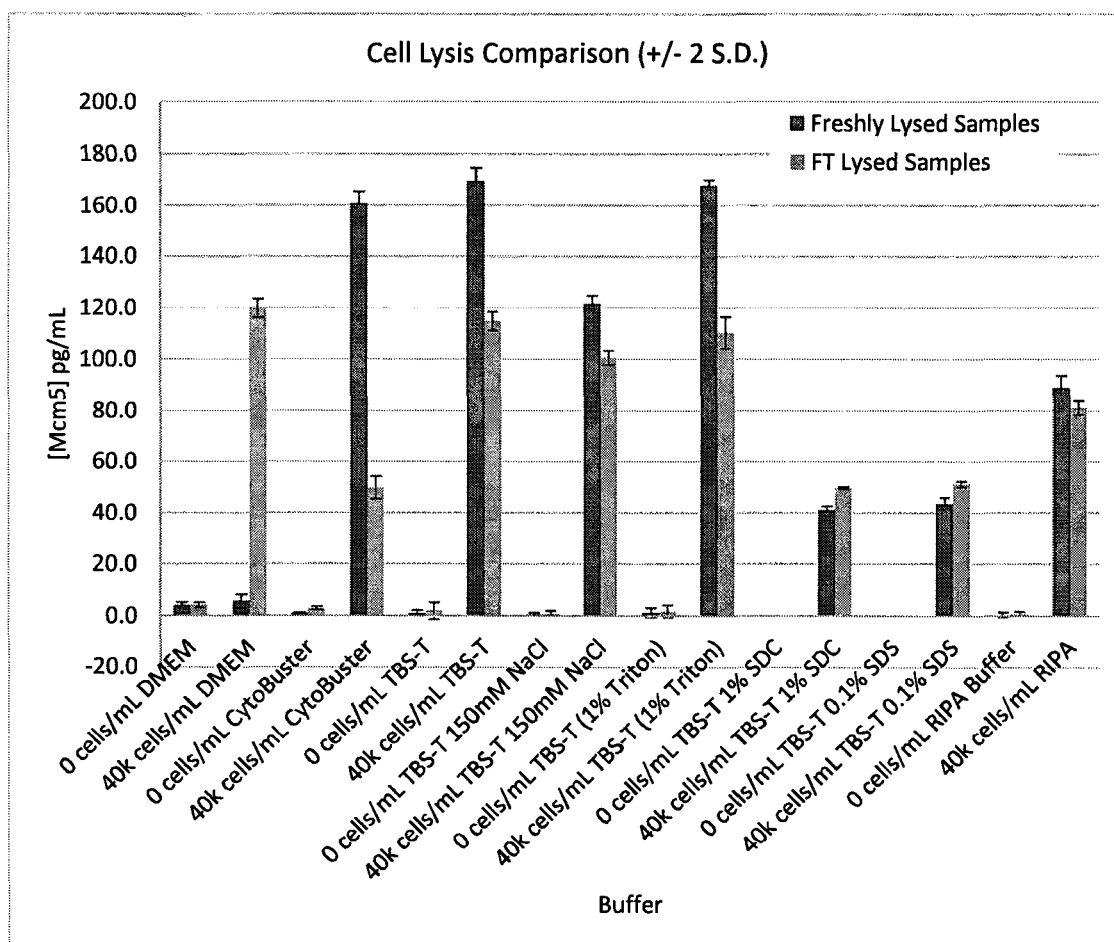
FIG. 6 shows a graph comparing buffers based on TBST Buffer and comprising elements from RIPA buffer, Pre- & Post-Lysate Freeze-Thaw.

Additional components were added to TBST to try to improve stability of TBST lysates. The potency of Mcm5 in the lysed samples was tested after application of buffer to both fresh and frozen cells. The results of this experiment are presented in FIG. 6.

Figure 7:
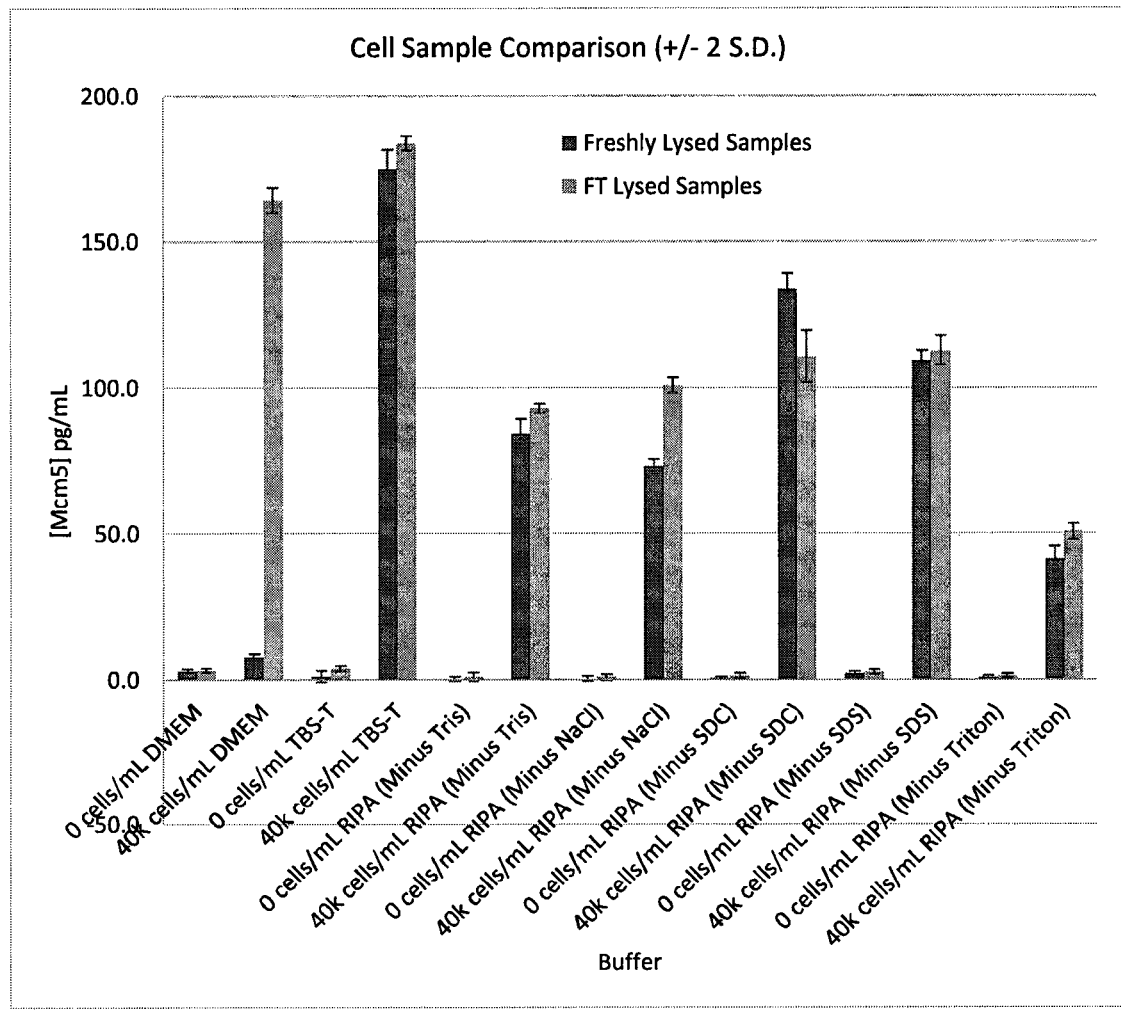
FIG. 7 shows a graph comparing buffers based on RIPA buffer but having some RIPA buffer elements removed, Pre- & Post-Lysate Freeze-Thaw.

These data (described in FIG. 6) demonstrated that the stabilising components of the RIPA buffer are the sodium deoxycholate (SDC) and the sodium dodecyl sulfate (SDS), but unfortunately the incorporation of these elements into the simpler TBST buffer cause a dramatic loss in signal. A supplemental test was performed to remove elements of the RIPA buffer one-by-one to see if removal of any element could improve the RIPA signal to the same level as the TBST while retaining stability. The results are described in FIG. 7.

Example 6

Figure 8:
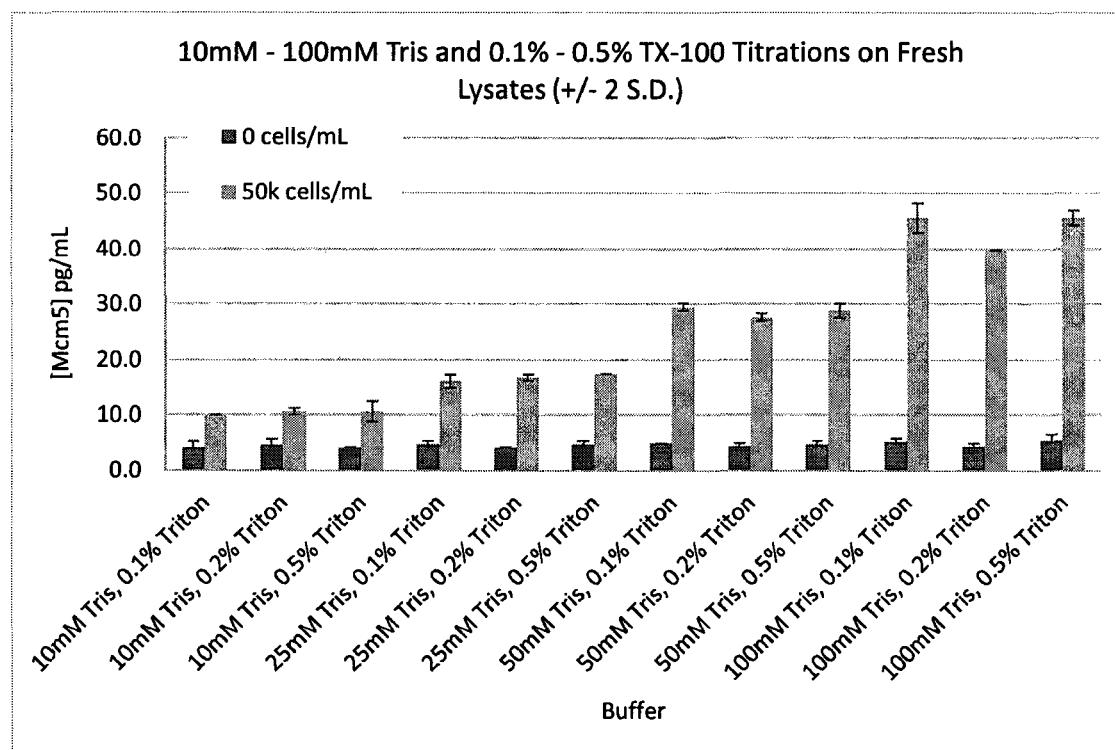
FIG. 8 shows a graph comparing buffers having different concentrations of Tris and TRITON™ X-100 (polyethylene glycol p-(1,1,3,3-tetramethylbutyl)-phenyl ether), using Fresh Lysates.

Various buffers comprising differing concentrations of Tris and TRITON™ X-100 were compared. The potency of Mcm5 in the lysed samples was tested after application of buffer to both fresh and frozen cells. The results are presented in FIG. 8.

The data showed that increasing the Tris concentration caused an improvement on cell lysate Mcm5 levels, although increasing the TRITON™ X-100 concentration had no effect.

Figure 9:
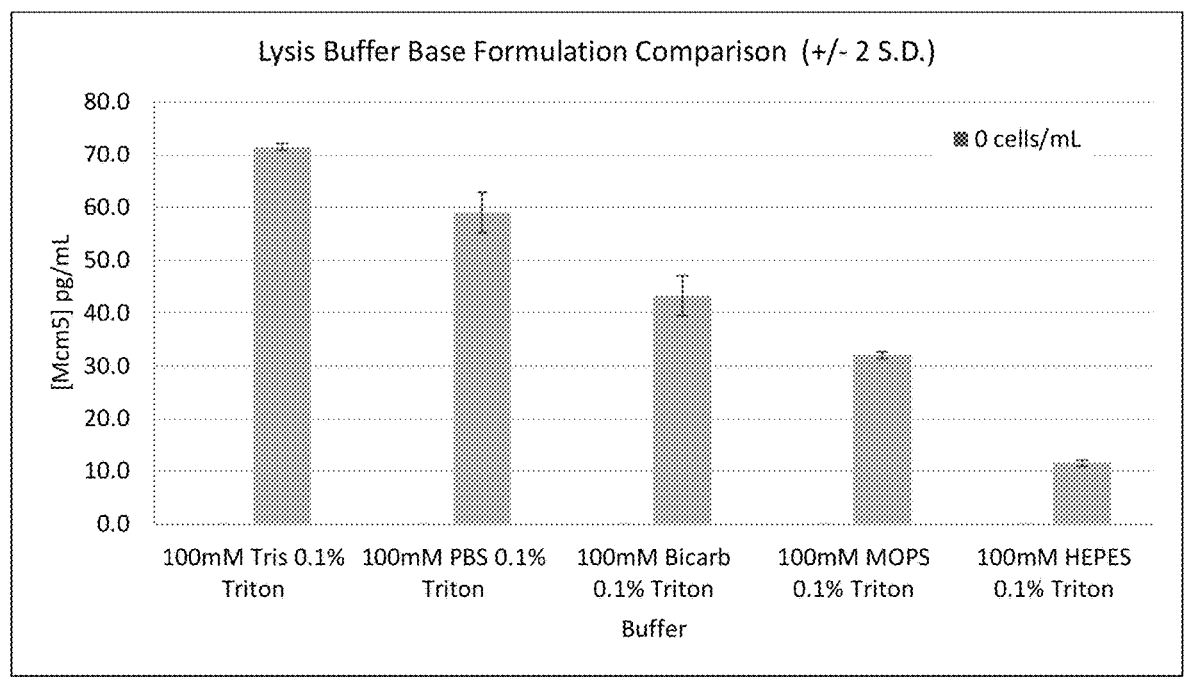
FIG. 9 shows a graph comparing different buffer base formulations (TBS, PBS, Bicarbonate, MOPS & HEPES), using Fresh Lysates.

To ensure the optimal base for the lysis buffer is used before progressing further, several compounds were tested across various pH ranges and buffer types. Several of these buffers gave good results, but TBS was shown to have the highest signal. These data are described in FIG. 9.

Example 7

Figure 10:
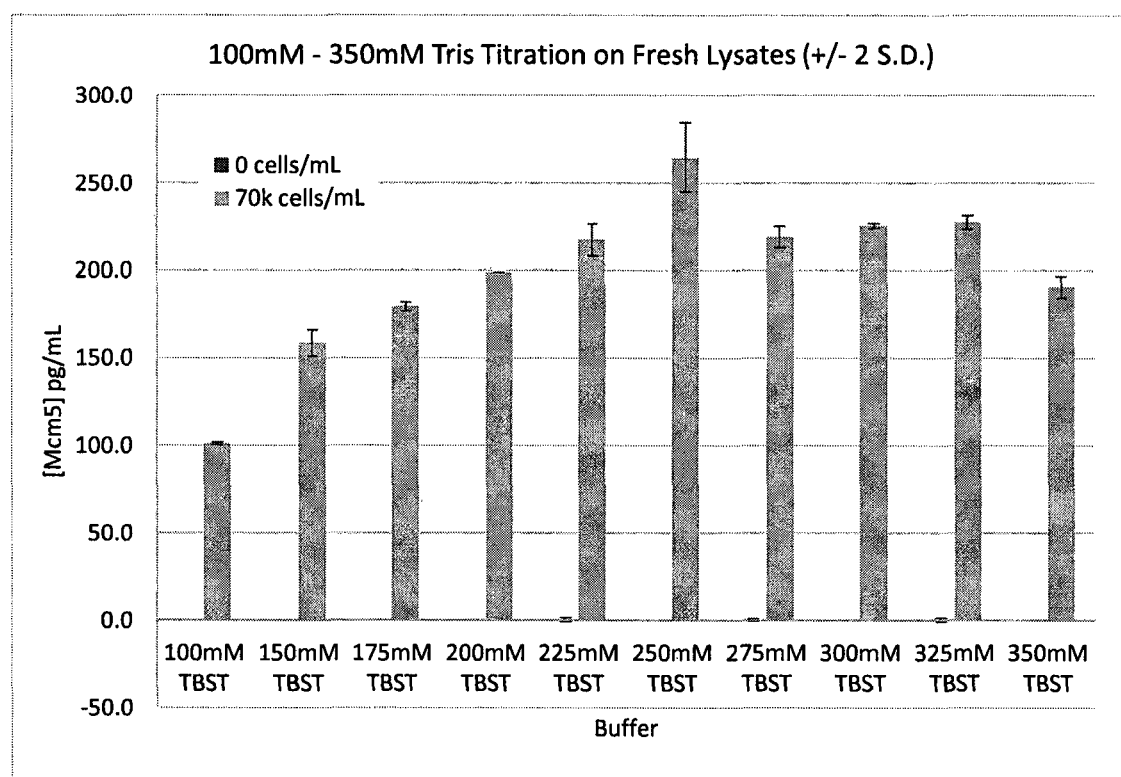
FIG. 10 shows a graph comparing buffers having different concentrations of Tris (100 mM-350 mM), using Fresh Lysates.

A further titration of Tris was performed to see whether the signal would still increase if a higher buffer concentration was used, and to see where the improvement plateaued. The results are presented in FIG. 10.

The level of Mcm5 begins to plateau at 225 mM Tris, with only the 250 mM Tris being higher, and then the signal is stable until 325 mM, after which a decrease is seen. To avoid potential issues with manufacturing and variation, a concentration on a stable area of the plateau would be the optimal choice, such as 300 mM.

Example 8

Figure 11:
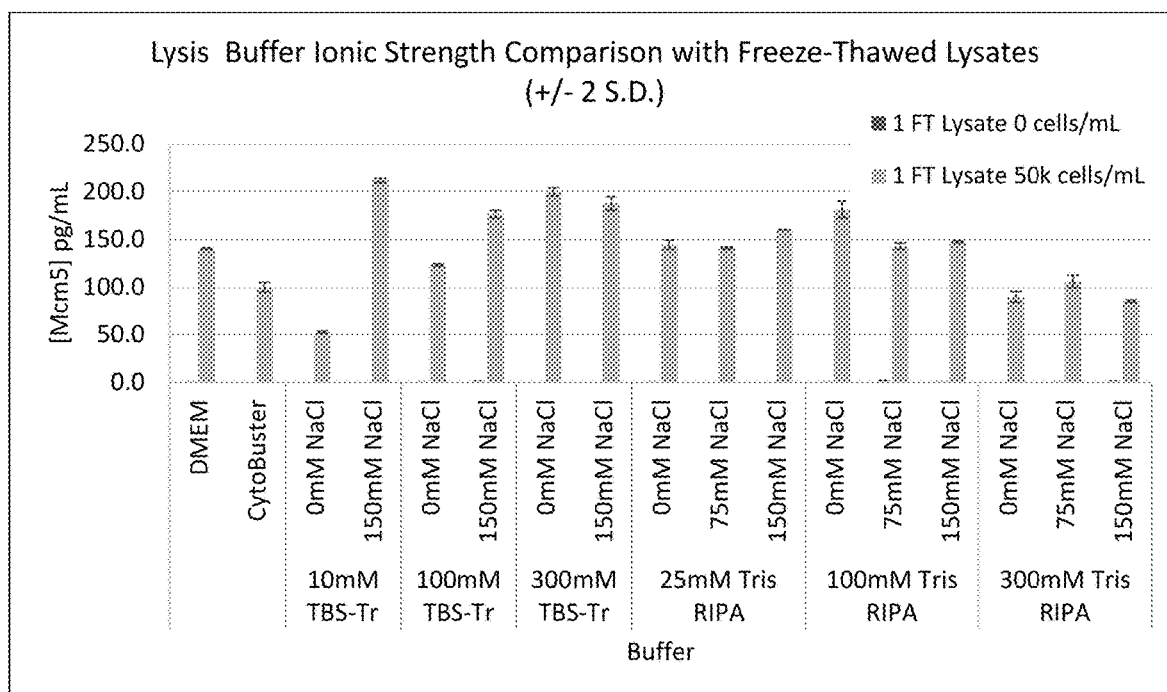
FIG. 11 shows a graph comparing buffers based on TBS-T and RIPA buffers but having altered ionic strength, using Freeze-Thawed Lysates.

It was hypothesised that altering the Tris concentration may be effective due to increased ionic strength. Since this can be equally achieved by adding NaCl, compositions having different concentrations of NaCl were tested. The results are presented in FIG. 11.

The data shows that increasing the NaCl concentration in TBST (TBS+TRITON™ X-100) buffers with lower Tris levels improves signal, but the same effect is not seen in RIPA buffer, regardless of the Tris concentration. Increasing the Tris concentration does not seem to have any substantial improvement on standard RIPA buffer (25 mM Tris and 150 mM NaCl) signal even if the NaCl level is reduced in compensation. The 10 mM Tris 150 mM NaCl TBST has the highest signal obtained in the data set (approximately double that of the CYTOBUSTER™ Protein Extraction Reagent), so this buffer was optimised in terms of NaCl concentration and assessed separately for stabilising components.

Example 9

Figure 12:
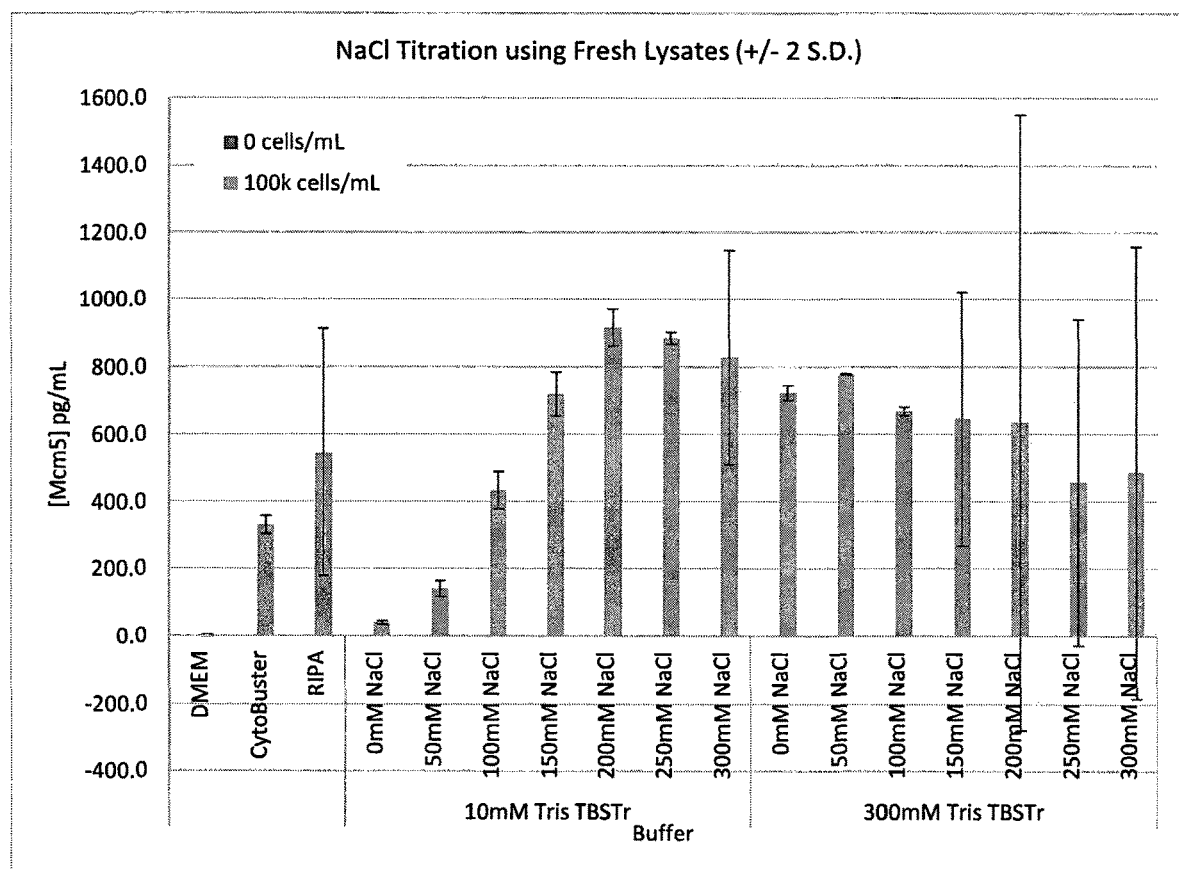
FIG. 12 shows a graph comparing TBS-T buffers having altered NaCl strength, using Freeze-Thawed Lysates.

The data presented in Example 8 suggests buffers having around 10 mM tris are most effective, so buffers having 10 mM tris and different NaCl concentrations were investigated. The results are presented in FIG. 12.

The titration of NaCl shows the best candidate to be the 10 mM Tris with 200 mM NaCl. The data also seems to show that when the ionic strength reaches a certain point, precision is compromised. The chosen formulation of the buffer from this point was 10 mM Tris, 200 mM NaCl & 0.1% TRITON™ X-100, to which stabilising compounds were then added to find a suitable final formulation.

Example 10

Various stabilisers were tested for tested for their effectiveness in stabilising the Mcm5 samples when combined with TBS-T.

Figure 13A:
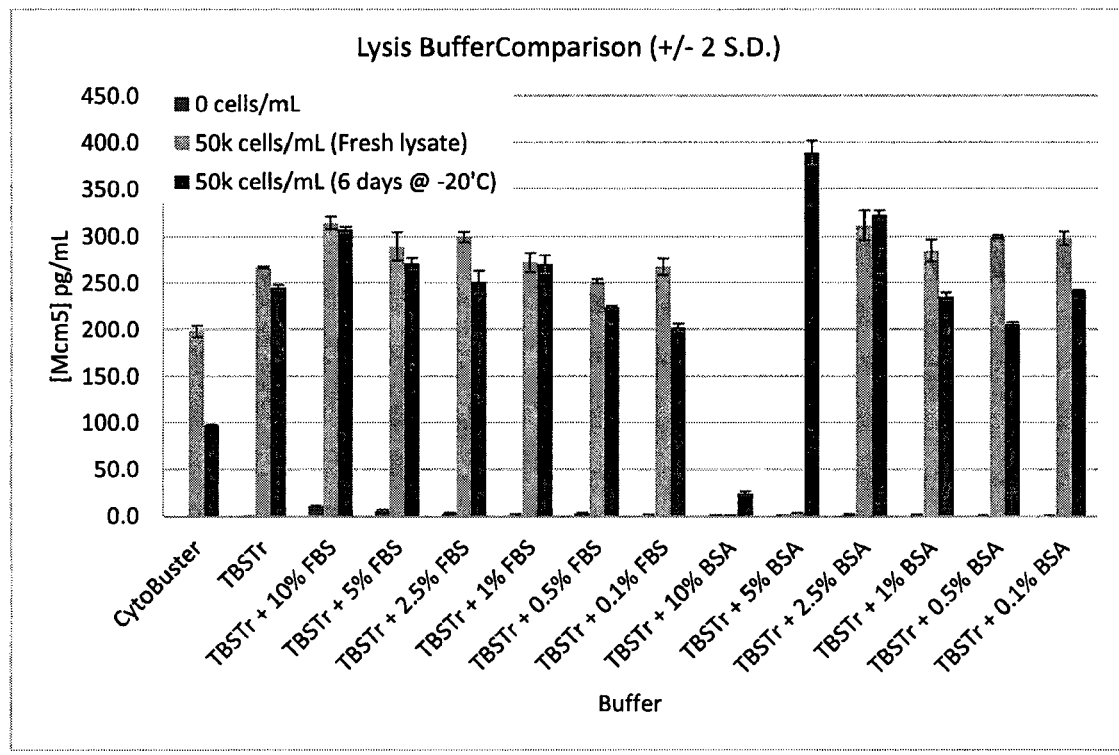
FIGS. 13A and 13B show graphs comparing TBS-T buffers which further comprise various stabilising agents.
Figure 13B:
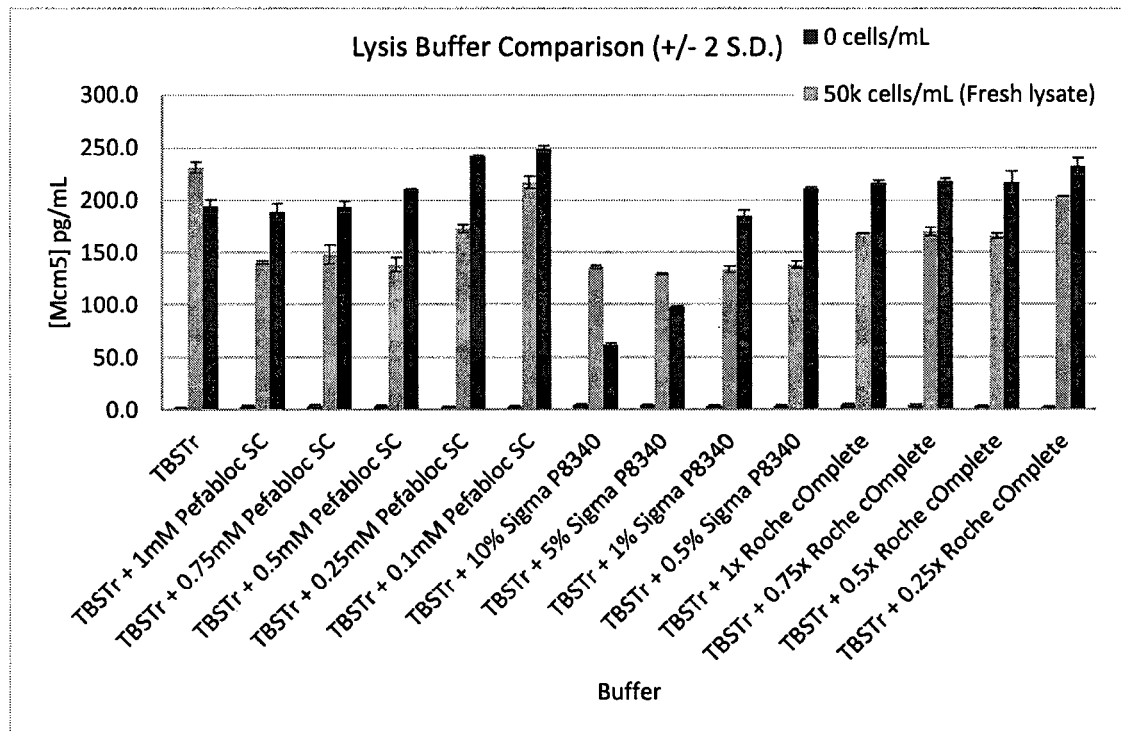

In terms of potential candidates, the 1% FBS (foetal bovine serum), 2.5% BSA (bovine serum albumin), 0.25 mM PEFABLOC® SC, 0.1 mM PEFABLOC® SC, 0.5% Sigma P8340 protease inhibitor cocktail and the 0.25× Roche COMPLETE™ protease inhibitor cocktail all had encouraging data without compromising the background or positive sample signal compared to the buffer without stability additives. These data are presented in FIGS. 13A and 13B.

Figure 14:
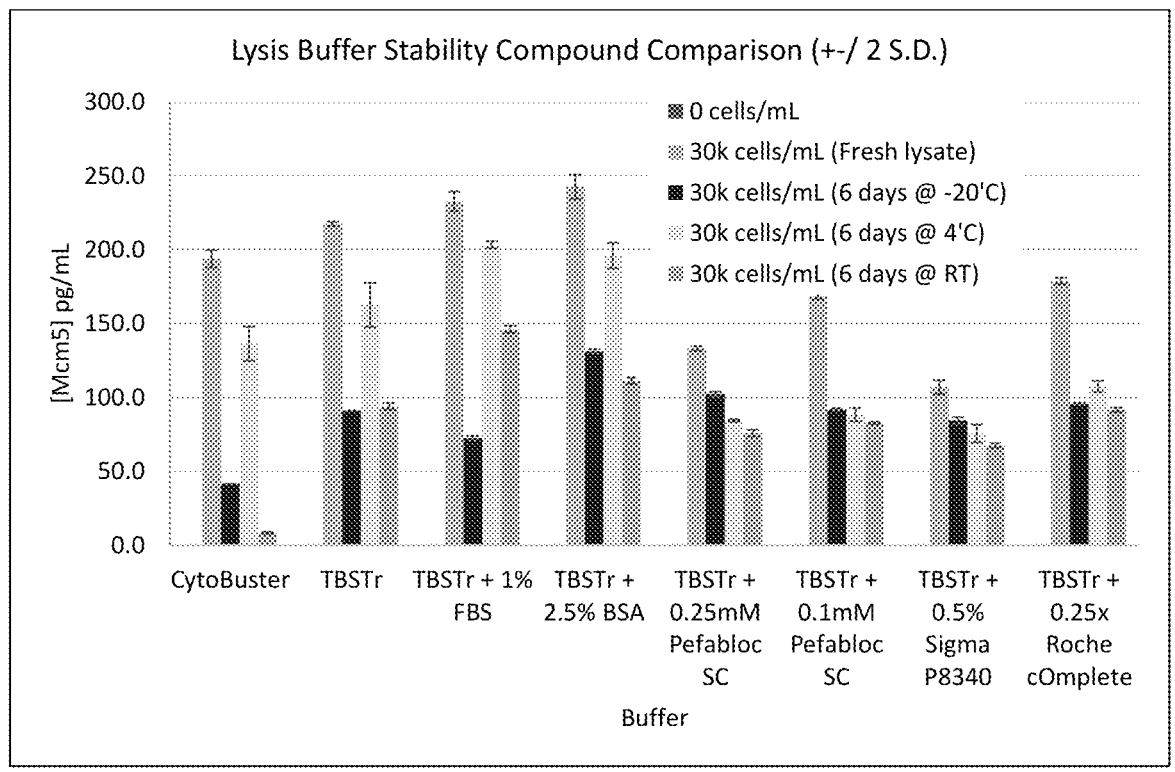
FIG. 14 shows a graph comparing TBST buffers comprising different concentrations of Stabilising Agents, after 6 Days Storage.

These compounds were tested with various storage temperatures after 6 days to see how they compared to the additive-free TBST and the CYTOBUSTER™ Protein Extraction Reagent. These data are presented in FIG. 14.

All the stabilisers were effective at stabilising the compositions. The commercially produced protease inhibitor cocktails (PEFABLOC® SC, Sigma P3840 & Roche COMPLETE™) were stable, but reduced the Mcm5 signal. The 2.5% BSA performed better than the 1% FBS at −20° C. Performance at 4° C. and fresh were equivalent for 1% FBS and 2.5% BSA, and both seem to increase signal comparison to standard TBST buffer. As there was a loss at −20° C. for the BSA, a repeat experiment was performed using additional cell lines to confirm the improvement to stability.

Example 11

Figure 15A:
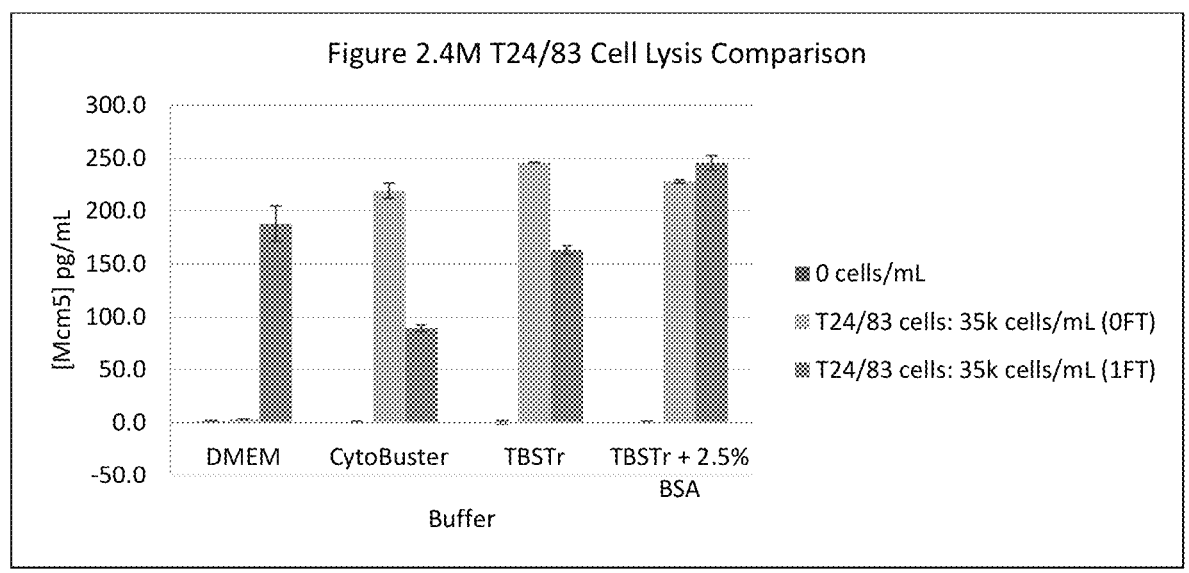
FIGS. 15A, 15B and 15C show graphs assessing the efficacy of TBST Buffer+/−2.5% BSA in various cell lines.
Figure 15B:
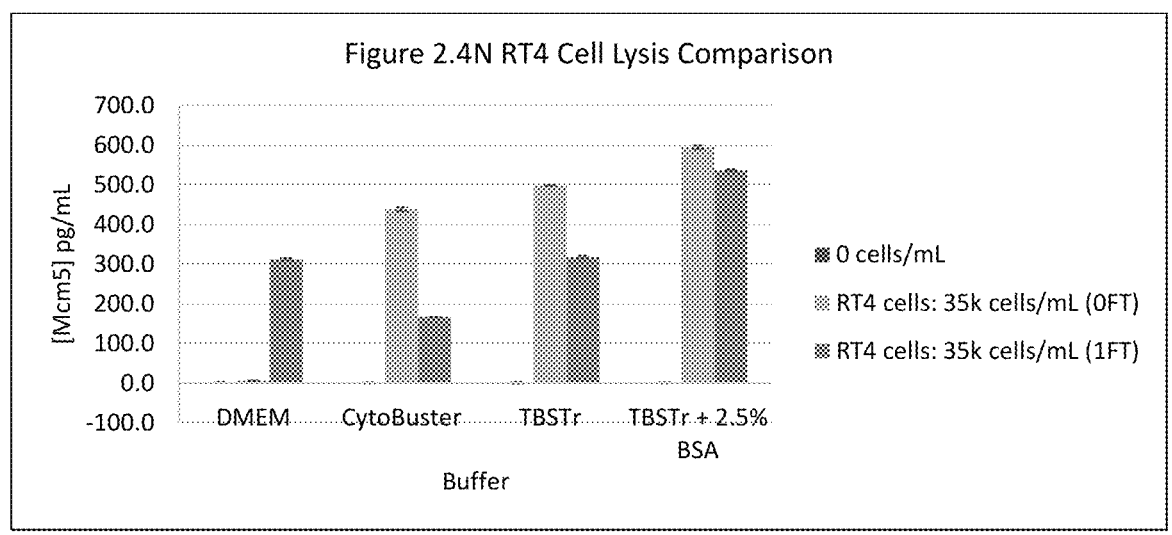
Figure 15C:
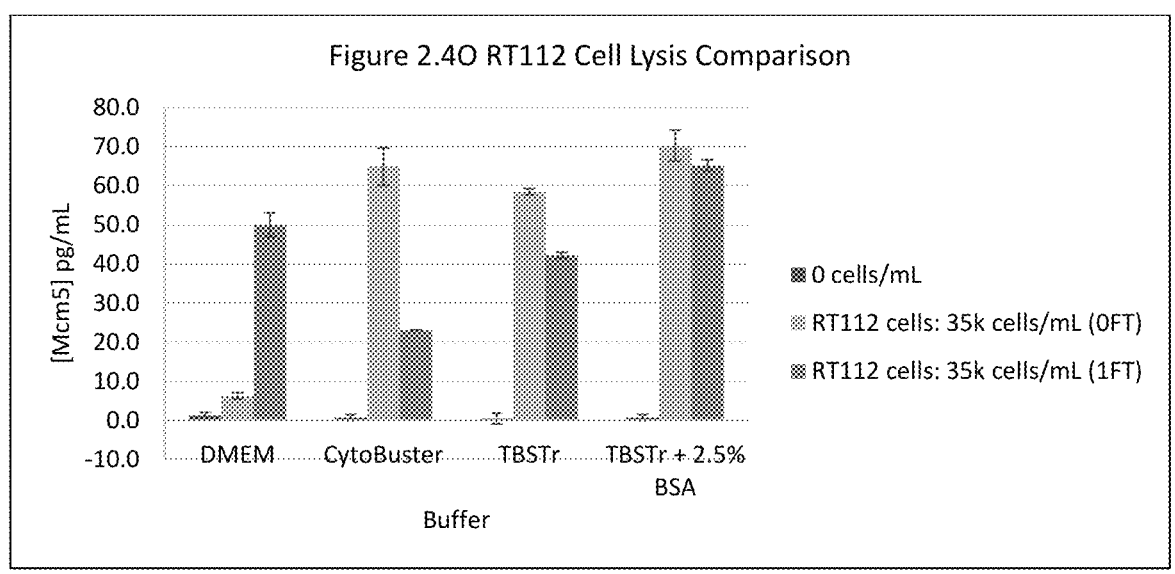

A TBSTr+2.5% BSA composition was compared with TBSTr and CYTOBUSTER™ Protein Extraction Reagent. The results are presented in FIGS. 15A, 15B and 15C.

With all cell lines, the TBST+2.5% BSA has proven to be both stable (concentration within 10% of fresh lysate) and to have the highest signal after 1 FT cycle than both CYTOBUSTER™ Protein Extraction Reagent and TBST. Generally speaking, CYTOBUSTER™ Protein Extraction Reagent appears to give very variable results with fresh lysates, but there is always a pronounced loss of potency when freeze-thawing is performed.

Example 12

Figure 16:
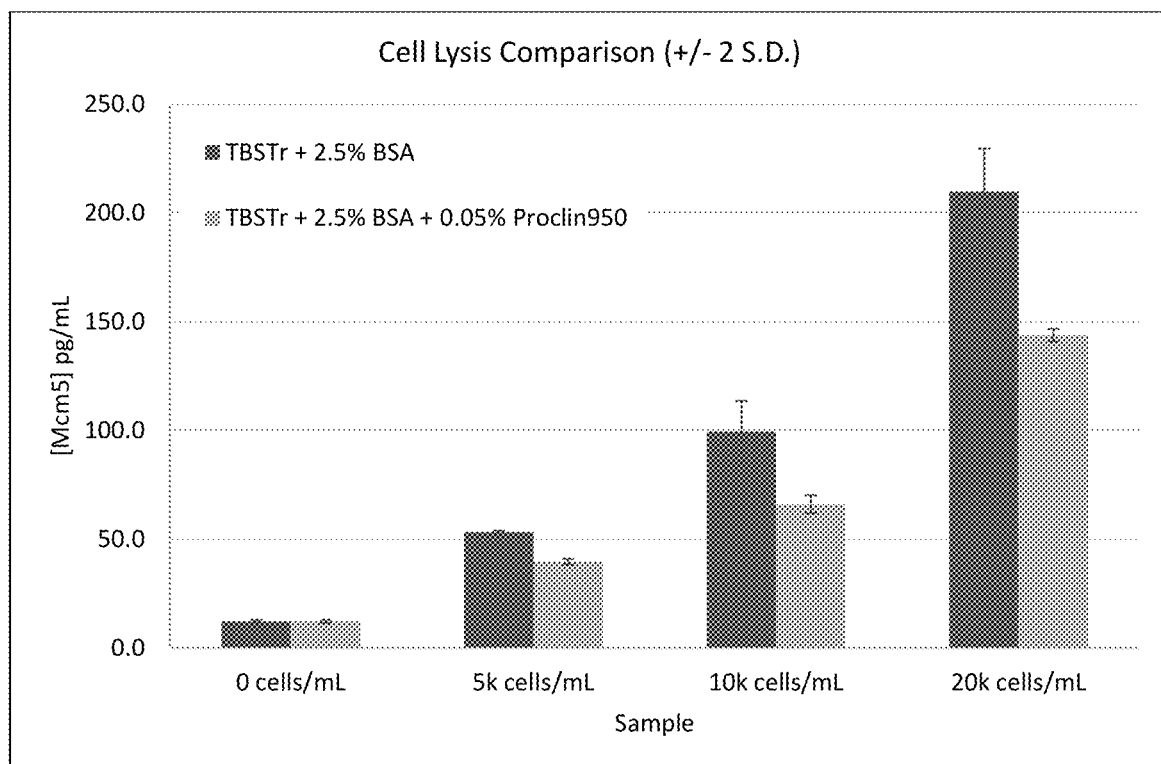
FIG. 16 shows a graph comparing TBST+2.5% BSA buffers with or without PROCLIN™ 950 (2-methyl-4-isothiazolin-3-one solution).
Figure 17:
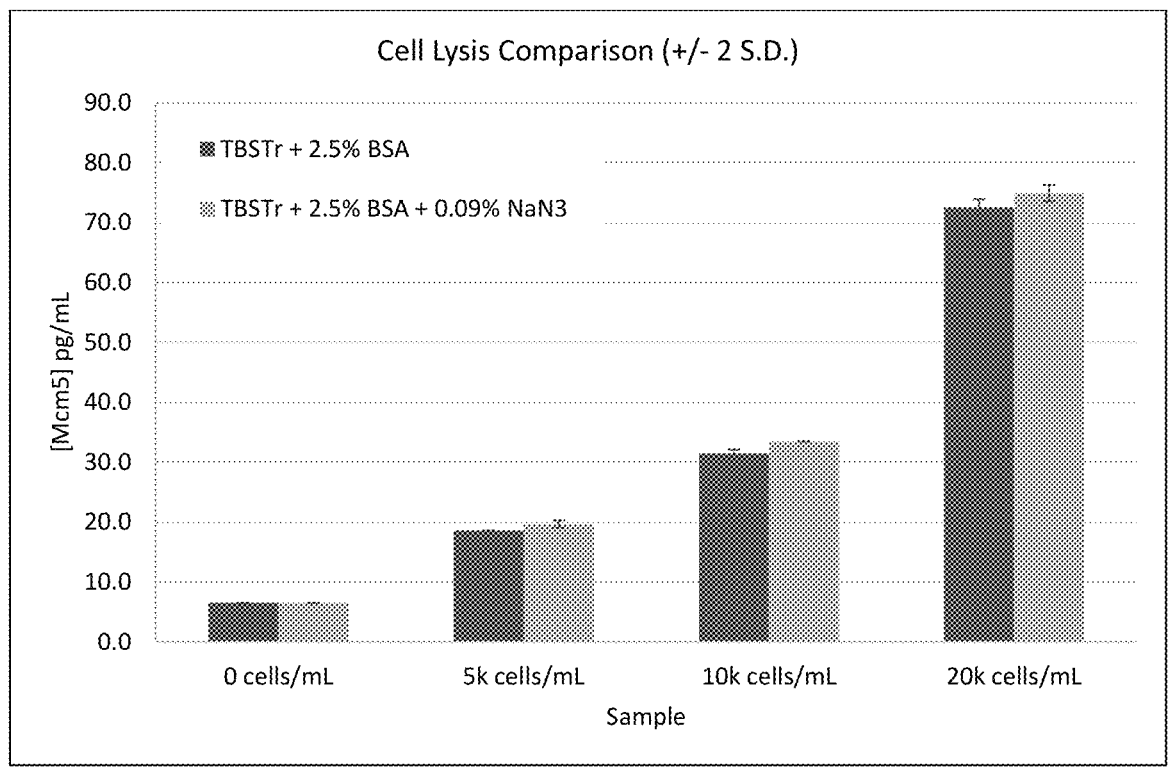
FIG. 17 shows a graph comparing TBST+2.5% BSA buffers with or without Sodium Azide (NaN3).

As BSA containing buffers tend to be prone to microbial growth, the two anti-microbial agents PROCLIN™ 950 and sodium azide (NaN3) were tested with the TBST+2.5% BSA formulation. The results are presented in FIGS. 16 and 17.

The 0.09% sodium azide is the best candidate for anti-microbial agent as there is less than 10% deviation from the reference buffer.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

SEQUENCE LISTING

<160> NUMBER OF SEQ ID NOS: 2

<210> SEQ ID NO 1
<211> LENGTH: 734
<212> TYPE: PRT
<213> ORGANISM: Homo sapiens
<220> FEATURE:
<223> OTHER INFORMATION: Mcm5 (polypeptide)

<400> SEQUENCE: 1

```
Met Ser Gly Phe Asp Asp Pro Gly Ile Phe Tyr Ser Asp Ser Phe Gly
1               5                   10                  15

Gly Asp Ala Gln Ala Asp Glu Gly Gln Ala Arg Lys Ser Gln Leu Gln
            20                  25                  30

Arg Arg Phe Lys Glu Phe Leu Arg Gln Tyr Arg Val Gly Thr Asp Arg
        35                  40                  45

Thr Gly Phe Thr Phe Lys Tyr Arg Asp Glu Leu Lys Arg His Tyr Asn
    50                  55                  60

Leu Gly Glu Tyr Trp Ile Glu Val Glu Met Glu Asp Leu Ala Ser Phe
65                  70                  75                  80

Asp Glu Asp Leu Ala Asp Tyr Leu Tyr Lys Gln Pro Ala Glu His Leu
                85                  90                  95

Gln Leu Leu Glu Glu Ala Ala Lys Glu Val Ala Asp Glu Val Thr Arg
            100                 105                 110

Pro Arg Pro Ser Gly Glu Glu Val Leu Gln Asp Ile Gln Val Met Leu
        115                 120                 125

Lys Ser Asp Ala Ser Pro Ser Ser Ile Arg Ser Leu Lys Ser Asp Met
    130                 135                 140

Met Ser His Leu Val Lys Ile Pro Gly Ile Ile Ile Ala Ala Ser Ala
145                 150                 155                 160

Val Arg Ala Lys Ala Thr Arg Ile Ser Ile Gln Cys Arg Ser Cys Arg
                165                 170                 175

Asn Thr Leu Thr Asn Ile Ala Met Arg Pro Gly Leu Glu Gly Tyr Ala
            180                 185                 190

Leu Pro Arg Lys Cys Asn Thr Asp Gln Ala Gly Arg Pro Lys Cys Pro
        195                 200                 205

Leu Asp Pro Tyr Phe Ile Met Pro Asp Lys Cys Lys Cys Val Asp Phe
    210                 215                 220

Gln Thr Leu Lys Leu Gln Glu Leu Pro Asp Ala Val Pro His Gly Glu
225                 230                 235                 240

Met Pro Arg His Met Gln Leu Tyr Cys Asp Arg Tyr Leu Cys Asp Lys
                245                 250                 255

Val Val Pro Gly Asn Arg Val Thr Ile Met Gly Ile Tyr Ser Ile Lys
            260                 265                 270

Lys Phe Gly Leu Thr Thr Ser Arg Gly Arg Asp Arg Val Gly Val Gly
        275                 280                 285

Ile Arg Ser Ser Tyr Ile Arg Val Leu Gly Ile Gln Val Asp Thr Asp
    290                 295                 300

Gly Ser Gly Arg Ser Phe Ala Gly Ala Val Ser Pro Gln Glu Glu Glu
305                 310                 315                 320

Glu Phe Arg Arg Leu Ala Ala Leu Pro Asn Val Tyr Glu Val Ile Ser
                325                 330                 335

Lys Ser Ile Ala Pro Ser Ile Phe Gly Gly Thr Asp Met Lys Lys Ala
            340                 345                 350

Ile Ala Cys Leu Leu Phe Gly Gly Ser Arg Lys Arg Leu Pro Asp Gly
```

355                 360                 365
Leu Thr Arg Arg Gly Asp Ile Asn Leu Leu Met Leu Gly Asp Pro Gly
370                 375                 380

Thr Ala Lys Ser Gln Leu Leu Lys Phe Val Glu Lys Cys Ser Pro Ile
385                 390                 395                 400

Gly Val Tyr Thr Ser Gly Lys Gly Ser Ser Ala Ala Gly Leu Thr Ala
                    405                 410                 415

Ser Val Met Arg Asp Pro Ser Ser Arg Asn Phe Ile Met Glu Gly Gly
                420                 425                 430

Ala Met Val Leu Ala Asp Gly Gly Val Val Cys Ile Asp Glu Phe Asp
            435                 440                 445

Lys Met Arg Glu Asp Asp Arg Val Ala Ile His Glu Ala Met Glu Gln
450                 455                 460

Gln Thr Ile Ser Ile Ala Lys Ala Gly Ile Thr Thr Thr Leu Asn Ser
465                 470                 475                 480

Arg Cys Ser Val Leu Ala Ala Ala Asn Ser Val Phe Gly Arg Trp Asp
                485                 490                 495

Glu Thr Lys Gly Glu Asp Asn Ile Asp Phe Met Pro Thr Ile Leu Ser
                500                 505                 510

Arg Phe Asp Met Ile Phe Ile Val Lys Asp Glu His Asn Glu Glu Arg
            515                 520                 525

Asp Val Met Leu Ala Lys His Val Ile Thr Leu His Val Ser Ala Leu
530                 535                 540

Thr Gln Thr Gln Ala Val Glu Gly Glu Ile Asp Leu Ala Lys Leu Lys
545                 550                 555                 560

Lys Phe Ile Ala Tyr Cys Arg Val Lys Cys Gly Pro Arg Leu Ser Ala
                565                 570                 575

Glu Ala Ala Glu Lys Leu Lys Asn Arg Tyr Ile Ile Met Arg Ser Gly
                580                 585                 590

Ala Arg Gln His Glu Arg Asp Ser Asp Arg Arg Ser Ser Ile Pro Ile
            595                 600                 605

Thr Val Arg Gln Leu Glu Ala Ile Val Arg Ile Ala Glu Ala Leu Ser
610                 615                 620

Lys Met Lys Leu Gln Pro Phe Ala Thr Glu Ala Asp Val Glu Glu Ala
625                 630                 635                 640

Leu Arg Leu Phe Gln Val Ser Thr Leu Asp Ala Ala Leu Ser Gly Thr
                645                 650                 655

Leu Ser Gly Val Glu Gly Phe Thr Ser Gln Glu Asp Gln Glu Met Leu
                660                 665                 670

Ser Arg Ile Glu Lys Gln Leu Lys Arg Arg Phe Ala Ile Gly Ser Gln
            675                 680                 685

Val Ser Glu His Ser Ile Ile Lys Asp Phe Thr Lys Gln Lys Tyr Pro
690                 695                 700

Glu His Ala Ile His Lys Val Leu Gln Leu Met Leu Arg Arg Gly Glu
705                 710                 715                 720

Ile Gln His Arg Met Gln Arg Lys Val Leu Tyr Arg Leu Lys
                725                 730

<210> SEQ ID NO 2
<211> LENGTH: 2534
<212> TYPE: DNA
<213> ORGANISM: Homo sapiens
<220> FEATURE:
<223> OTHER INFORMATION: Mcm5 (mRNA)

<400> SEQUENCE: 2

```
ggaaaaccag aggcgcagtc atgtcgggat tcgacgatcc tggcatttc tacagcgaca      60
gcttcggggg cgacgcccag gccgacgagg ggcaggcccg caaatcgcag ctgcagaggc    120
gcttcaagga gttcctgcgg cggtaccgag tgggcaccga ccgcacgggc ttcaccttca    180
aatacaggga tgaactcaag cggcattaca acctggggga gtactggatt gaggtggaga    240
tggaggatct ggccagcttt gatgaggacc tggccgacta cttgtacaag cagccagccg    300
agcacctgca gctgctggag gaagctgcca aggaggtagc tgatgaggtg acccggcccc    360
ggccttctgg ggaggaggtg ctccaggaca tccaggtcat gctcaagtcg acgccagcc    420
cttccagcat tcgtagcctg aagtcggaca tgatgtcaca cctggtgaag atccctggca    480
tcatcatcgc ggcctctgcg gtccgtgcca aggccaccg catctctatc cagtgccgca    540
gctgccgcaa caccctcacc aacattgcca tgcgccctgg cctcgagggc tatgccctgc    600
ccaggaagtg caacacagat caggctgggc gccccaaatg cccattggac ccgtacttca    660
tcatgcccga caaatgcaaa tgcgtggact tccagaccct gaagctgcag agctgcctg    720
atgcagtccc ccacggggag atgcccagac acatgcagct ctactgcgac aggtacctgt    780
gtgacaaggt cgtccctggg aacagggtta ccatcatggg catctactcc atcaagaagt    840
ttggcctgac taccagcagg ggccgtgaca gggtgggcgt gggcatccga agctcctaca    900
tccgtgtcct gggcatccag gtggacacag atggctctgg ccgcagcttt gctggggccg    960
tgagccccca ggaggaggag gagttccgtc gcctggctgc cctcccaaat gtctatgagg   1020
tcatctccaa gagcatcgcc ccctccatct ttggggcac agacatgaag aaggccattg   1080
cctgcctgct ctttggggc tcccgaaaga ggctccctga tggacttact cgccgaggag   1140
acatcaacct gctgatgcta ggggaccctg ggacagccaa gtcccagctt ctgaagtttg   1200
tggagaagtg ttctcccatt ggggtataca cgtctgggaa aggcagcagc gcagctggac   1260
tgacagcctc ggtgatgagg gacccttcgt cccggaattt catcatggag ggcggagcca   1320
tggtcctggc cgatggtggg gtcgtctgta ttgacgagtt tgacaagatg cgagaagatg   1380
accgtgtggc aatccacgaa gccatggagc agcagaccat ctctatcgcc aaggctggga   1440
tcaccaccac cctgaactcc cgctgctccg tcctggctgc tgccaactca gtgttcggcc   1500
gctgggatga cgaaggggg gaggacaaca ttgacttcat gcccaccatc ttgtcgcgct   1560
tcgacatgat cttcatcgtc aaggatgagc acaatgagga gagggatgtg atgctggcca   1620
agcatgtcat cactctgcac gtgagcgcac tgacacagac acaggctgtg gagggcgaga   1680
ttgacctggc caagctgaag aagtttattg cctactgccg agtgaagtgt ggccccccggc   1740
tgtcagcaga ggctgcagag aaactgaaga accgctacat catcatgcgg agcgggggccc   1800
gtcagcacga gagggacagt gaccgccgct ccagcatccc catcactgtg cggcagctgg   1860
aggccattgt gcgcatcgcg gaagccctca gcaagatgaa gctgcagccc ttcgccacag   1920
aggcagatgt ggaggaggcc ctgcggctct tccaagtgtc cacgttggat gctgccttgt   1980
ccggtaccct gtcaggggtg gagggcttca ccagccagga ggaccaggag atgctgagcc   2040
gcatcgagaa gcagctcaag cgccgctttg ccattggctc ccaggtgtct gagcacagca   2100
tcatcaagga cttcaccaag cagaaatacc cggagcacgc catccacaag gtgctgcagc   2160
tcatgctgcg gcgcggcgag atccagcatc gcatgcagcg caaggttctc taccgcctca   2220
agtgagtcgc gccgcctcac tggactcatg gactcgccca cgcctcgccc ctcctgccgc   2280
tgcctgccat tgacaatgtt gctgggacct ctgcctcccc actgcagccc tcgaacttcc   2340
```

```
caggcaccct cctttctgcc ccagaggaag gagctgtagt gtcctgctgc ctctgggcgc    2400
ccgcctctag cgcggttctg ggaagtgtgc ttttggcatc cgttaataat aaagccacgg    2460
tgtgttcagg taaaaaaaaa aaaaaaaaaa aaaaaaaaaa aaaaaaaaaa aaaaaaaaaa    2520
aaaaaaaaaa aaaa                                                      2534
```

The invention claimed is:

1. A method for analysing a urine sample from a subject comprising:
   a. exposing the urine sample to a lysis buffer wherein the lysis buffer is capable of releasing a minichromosome maintenance (Mcm) protein from cells in the urine sample, wherein the lysis buffer comprises (i) a detergent which comprises or consists of polyethylene glycol p-(1,1,3,3-tetramethylbutyl)-phenyl ether, and (ii) a buffer component which comprises or consists of tris(hydroxymethyl)methylamine or tris(hydroxymethyl)methylamine hydrochloride; and wherein the Mcm protein is Mcm5; and
   b. performing an enzyme-linked immunosorbent assay (ELISA) to determine the concentration of Mcm5 in the urine sample.

2. The method of claim 1 wherein
   a. the lysis buffer is not PBS containing 0.4% sodium deoxycholate and 0.02% sodium azide;
   b. the method does not comprise incubation of the urine sample at a temperature greater than 90° C. for greater than 45 minutes;
   c. the method does not comprise shearing nucleic acids in the urine sample by passing the urine sample through a 21 gauge needle;
   d. the method does not comprise digesting the nucleic acids by exposing the urine sample to DNase I or RNase A; and/or
   e. the method does not comprise centrifuging the sample at 15,000 g for 10 minutes.

3. The method of claim 1 wherein:
   (i) the lysis buffer is capable of releasing Mcm5 from cells in the urine sample and does not substantially denature the Mcm5 protein;
   (ii) the method is a method for releasing Mcm5 from cells in the urine sample and determining the concentration of Mcm5 released from the cells;
   (iii) the method comprises a step of concentrating cells in the urine sample prior to the step of exposing the urine sample to a lysis buffer, exposing the concentrated cells to lysis buffer or resuspension of the pelleted cells from the sample in a lysis buffer;
   (iv) the lysis buffer does not denature an antibody;
   (v) the detergent further comprises polyethylene glycol p-(1,1,3,3-tetramethylbutyl)-phenyl ether at a concentration between 0.01% and 25%, between 0.01% and 10%, between 0.05% and 5%, between 0.05% and 1%, between 0.05% and 0.5% or around 0.1%;
   (vi) the detergent further comprises sodium deoxycholate or sodium dodecylsulphate at a concentration between 0.1% and 20%, between 0.5% and 10%, between 0.5% and 5% or around 1%;
   (vii) the lysis buffer comprises sodium deoxycholate at a concentration between 0.01% and 0.15%, between 0.03% and 0.10%, between 0.05% and 0.09%, or about 0.08%;
   (viii) the buffer component comprises or consists of tris(hydroxymethyl)methylamine (Tris) buffer at a concentration greater than 5 mM, between 5 mM and 350 mM, between 200 mM and 300 mM, between 10 mM and 25 mM, around 10 mM or around 250 mM;
   (ix) the buffer component maintains the pH of the lysis buffer between pH 4 and pH 9, between pH 5 and pH 8, between pH 6 and pH 8 or around pH 7.6;
   (x) the lysis buffer comprises a salt selected from the group consisting of sodium chloride, potassium chloride, magnesium chloride, sodium sulphate, potassium sulphate, magnesium sulphate, sodium acetate, potassium acetate, magnesium acetate, sodium phosphate, potassium phosphate and magnesium phosphate;
   (xi) the lysis buffer comprises a salt which is at a concentration between 20 mM and 300 mM, between 150 mM and 300 mM, between 100 mM and 200 mM or around 200 mM;
   (xii) the lysis buffer has an ionic strength of between 1 mM and 500 mM, between 50 mM and 450 mM, between 100 mM and 250 mM, or between 100 mM and 175 mM;
   (xiii) the lysis buffer comprises radioimmunoprecipitation assay (RIPA) buffer;
   (xiv) the method does not comprise incubation of the urine sample at a high temperature;
   (xv) the method does not comprise incubation of the urine sample at a high temperature and the high temperature is a temperature greater than 50° C., greater than 60° C., greater than 70° C., greater than 80° C., between 50° C. and 120° C., between 60° C. and 110° C., between 70° C. and 100° C., or between 80° C. and 100° C.;
   (xvi) the method does not comprise incubation of the urine sample at a high temperature for more than 30 minutes, more than 35 minutes, more than 40 minutes, more than 45 minutes, between 30 minutes and 2 hours, between 35 minutes and 2 hours, or between 40 minutes and 2 hours;
   (xvii) the method does not comprise shearing nucleic acids in the urine sample by mechanical shearing;
   (xviii) the method does not comprise exposing the urine sample to enzymes which digest nucleic acids;
   (xvix) the method does not comprise centrifuging the sample at 15,000 g for 10 minutes;
   (xx) an abnormal value for the concentration of Mcm 5 indicates an increased likelihood of a urological cancer in the subject;
   (xxi) the method is a method for detecting the presence of a urological cancer in a subject;
   (xxii) the method is a method for detecting the presence of a urological cancer in a subject and the urological cancer is prostate, kidney and/or bladder cancer;
   (xxiii) the assay to determine the concentration of Mcm5 is a sandwich ELISA; and/or (xxiv) the assay to determine the concentration of Mcm5 is a sandwich ELISA which comprises capturing Mcm5 in the sample using a capture antibody and detecting the concentration of Mcm5 using a detection antibody, wherein the capture antibody and the detection antibody bind specifically Mcm5, optionally wherein the capture antibody is immobilised on an ELISA plate and/or the detection antibody is conjugated to Horse Radish Peroxidase.

4. The method of claim 1 wherein the detergent further comprises sodium deoxycholate or sodium dodecylsulphate.

5. The method of claim 1 wherein the lysis buffer comprises or consists of sodium chloride at a concentration between 20 mM and 300 mM, between 150 mM and 300 mM, between 100 mM and 200 mM or around 200 mM.

6. The method of claim 1 wherein the urine sample:
(i) comprises urinary sediment; and/or
(ii) comprises urinary sediment obtained from first catch urine collected after prostatic massage.

* * * * *